United States Patent [19]

Fukuhara et al.

[11] Patent Number: 5,139,935
[45] Date of Patent: Aug. 18, 1992

[54] METHOD OF REGULATING EXPRESSION OF A FOREIGN GENE BY CONTROLLING THE SUGAR CONCENTRATION IN A MEDIUM AND A PROCESS OF PRODUCING A FOREIGN PRODUCT THEREBY

[75] Inventors: Nobuhiro Fukuhara, Ohmuta; Setsuo Yoshino, Yokohama; Satori Sone, Yokohama; Yoshiyuki Nakajima, Yokohama; Nobuyoshi Makiguchi, Fujisawa, all of Japan

[73] Assignee: Mitsui Toatsu Chemicals, Incorporated, Tokyo, Japan

[21] Appl. No.: 659,472

[22] Filed: Feb. 25, 1991

Related U.S. Application Data

[63] Continuation of Ser. No. 156,586, Feb. 17, 1988, abandoned.

[30] Foreign Application Priority Data

Feb. 19, 1987 [JP] Japan .................................. 62-034396
Jun. 18, 1987 [JP] Japan .................................. 62-152358

[51] Int. Cl.$^5$ .......................... C12N 1/21; C12N 9/88; C12N 15/11; C12N 15/60
[52] U.S. Cl. ............................... 435/69.1; 435/172.3; 435/232; 435/252.33; 435/320.1; 935/29; 935/41; 935/42
[58] Field of Search ............... 435/252.33, 320.1, 69.1, 435/172.3; 935/9, 14, 29, 41, 73

[56] References Cited

U.S. PATENT DOCUMENTS

| | | | |
|---|---|---|---|
| 4,431,739 | 2/1984 | Riggs et al. | 435/253 |
| 4,704,362 | 11/1987 | Itakura et al. | 435/253 |
| 4,946,790 | 8/1990 | Fukuhara et al. | 435/252.33 |

FOREIGN PATENT DOCUMENTS

| | | |
|---|---|---|
| 0152613 | 8/1985 | European Pat. Off. |
| 0260919 | 3/1988 | European Pat. Off. |
| 8802024 | 3/1988 | PCT Int'l Appl. |

OTHER PUBLICATIONS

Gilbert et al J. of Bacterial. vol. 161 pp. 314-320 (1985).

Styer Biochemistry 2nd Edit 1982 p. 673-675.
Scaife et al Genetics of Bacteria 1985 pp. 264-267, 17-21.
Journal of Bacteriology, vol. 161, No. 1 Jan. 1985 "Molecular cloning of the phenlaline ammonia lyase gene from Rhodosporidium toruloides in *Escherichis coli* K-12" pp. 314-320—Gilbert et al.
Gene, vol. 58, nos. 2+3, 1987, pp. 189-199 Anson et al, "Complete nucleotide sequence of the Rhodosporidium toruloides gene coding for phenylalnine ammonia lyase".
Biotechnology, vol. 4, No. 9, Sep. 1986, pp. 802-808, Mieschendahl et al. "A novel prophage independent TRP regulated lambda P1 expression system."
Gene, vol. 15, 1981, pp. 81-93, Remaut et al "Plasmid vectors for high-efficiency expression controlled by the P1 promoter of coliphage lambda".

(List continued on next page.)

*Primary Examiner*—Robert A. Wax
*Assistant Examiner*—Dian Cook
*Attorney, Agent, or Firm*—Nixon & Vanderhye

[57] ABSTRACT

*Escherichia coli* carrying a hybrid plasmid having been constructed by inserting a desired foreign gene into an expression vector so as to permitting expression of said desired foreign gene therein was cultured in a medium containing a sugar component utilizable by the *E. coli* as a carbon source at a concentration of 0.3% or more so that the expression of said desired foreign gene was suppressed. This *E. coli* (i.e., transformant) was cultured in the medium in which the sugar concentration was maintained at 0.3% or more in a first process so as to supress the suppression of the foreign gene and to support sufficient cell growth and thereafter at less than 0.3% in a second process to release the suppression of the expression so as to permit effective production of the foreign gene product, which resulted in high concentration of the foreign gene product in the final culture.

4 Claims, 16 Drawing Sheets

OTHER PUBLICATIONS

Nucleic Acids Research, vol. 11, No. 14, 1983. pp. 4677–4688; Remaut et al "Inducible high level synthesis of mature human fibroblast interferon in *Escherichia coli*".

Methods in Enzymology, vol. 101, 1983, pp. 155–164; Nichols et al "Plasmids containing the trp promoters of *Escherichia coli* and *Serratia marcescens* and their use in expressing cloned genes".

Proceedings of the National Academic Science USA, vol. 80, Jan. 1983, pp. 21–25 Boer et al; "The tac promoter;/ A functional hybrid derived from the trp and lac promoters."

Gene, vol. 25, No. 2/3, Nov. 1983, pp. 167–178, Amann et al, "Vectors bearing a hybrid trp-lac promoter useful for regulated expression of cloned genes in *Escherichia coli*".

Lewin: "Genes" 1983, pp. 251–252, John Wiley, New York.

FIG. 2(A)

```
ATGGCACCCTCGCTCGACTCTCGCACTCGTTCCGCAAACGGGCGTCGCATCCGCAAAG       60
CAGGCTGTCAATGGCGCCTCGACCAAACCTCGCAGTCGCAGGCTCGCACCTGCCCACAACC  120
CAGGTCACGCAGGTCGACATCGTCGAGAAGATGCTCGCGCCGACTCGACGCTC          180
GAACTCGACGGCTACTCGCGCTCAACCCTCGGAGACGTCGTCTCGGCCGAGGAAGGGCAGG  240
CCTGTCCGCGTCAAGGACAGCGACGAGATCCGCTCAAAGATTGACAAATCGGTCGAGTTC  300
TTGCGCTCGCAACTCTCCATGAGCGTCTACGGCGTCACGACTGGATTTGGCGGATCCGCA  360
GACACCCGCACCGAGGAGGCCATCTCTCGCCCAGAAGGCTCTCCTCCGAGCACCAGCTCTGC  420
GGTGTTCTCCCTTCGTTCGACTTCGTTCCGCCCTCCGGCGGTCTCGGAGAACTCGCTT  480
CCCCCTCGAGGTTGTTCGCGGCCATGACAATCCGCGTCAACAGCTTGACCCGGCCAC    540
TCGGCTGTCCGCCTCGTCCCTCGAGGCTCACCAACTTCCTCAACTTCCTCAACGGCATCACC  600
```

FIG. 2(B)

```
         610        620        630        640        650        660
CCCATCGTCCCCCTCCGCGGGCACCATCTCTGCGTCGGGCGACCCTCTCCTCTCTCCTAC
         670        680        690        700        710        720
ATTGCAGCGGCCATCAGCGGTCACCCGGACAGCAAGGTGCACGTCGTCCACGAGGGCAAG
         730        740        750        760        770        780
GAGAAGATCCTGTACGCCGCGAGGGCGATGGCGCTCTTCAACCTCGAGCATCCCGTCGTCCCTC
         790        800        810        820        830        840
GGCCCCGAAGGAAGGTCTCGGTCTCGTCAACGGCACCGCGTCTCAGCATCGATGGCCACC
         850        860        870        880        890        900
CTCGCTCTGCACGACGCACACATGCTCTCGCTCCTCTCGCAGTCGCTCACGGCCATGACG
         910        920        930        940        950        960
GTCGAAGCGATGGTCGGCCACGCGGGCTCGTTCCACCCCTTCCTTCACGACGTCACGCGC
         970        980        990       1000       1010       1020
CCTCACCCGACGCAGATCGAAGTCGCGGGAAACATCCGCAAGCTCCTCGAGGGAAGCCGC
        1030       1040       1050       1060       1070       1080
TTTGCTGTCCACCATGAGGAGGAGGTCAAGGTCAAGGACGAGGGCATTCTCCGCCAG
        1090       1100       1110       1120       1130       1140
GACCGCTACCCCTTGCGCTCTCCTGGCTCGTCAGTGGCCCGGCTCGTCAGCCGACCTCATT
        1150       1160       1170       1180       1190       1200
CACGCCCACGGCCGTCCTCACCATCGAGGCCCGGCCAGTCGACGACCGACAACCCTCTCATC
```

FIG.2(C)

```
                 1210      1220      1230      1240      1250      1260
GACGTCGAGAACAAGACTTCGCACCACGGGCGGGCAATTTCCAGGCTGCCGCTGTGGCCAAC 1270      1280      1290      1300      1310      1320
ACCATGGAGAAGACTCGCCTCGGGCTCGCCCAGATCGGCAAGCTCAACTTCACGCAGCTC 1330      1340      1350      1360      1370      1380
ACCGAGATGCTCAACGCCGGCATGAACGCGGGCCTCCCCTGCCTCGCGGCCGAAGAC 1390      1400      1410      1420      1430      1440
CCCTCGCTCTCCTACCACTGCAAGGGCCTCGACATCGCCTGCGGTACACCTCGGAG 1450      1460      1470      1480      1490      1500
TTGGGACACCCTCGCCAACCTGTGACGACGCATGTCCAGCCGGGCTGAGATGGGCGAACCAG 1510      1520      1530      1540      1550      1560
GCGGTCAACTCGCGCTTGCGCTCATCTCGGCTCGTCGCACCGAGTCCAACGACGTCCTT 1570      1580      1590      1600      1610      1620
TCTCTCCTCCGCCACCACCTCTACTGCCGTTCTCCAAGCCATGCGACTTGCGGCGATC 1630      1640      1650      1660      1670      1680
GAGTTCGAGGTTCAAGAAGCAGTTCGGCTCGAACCTGTCTCCGTCATCGACCAGCACTTT 1690      1700      1710      1720      1730      1740
GGCTCCGCCATGACCGGCTCGAACCTGCGCGACGAGCTCGTCGAGAAGGTGAACAAGACG 1750      1760      1770      1780      1790      1800
CTCGCCAAGCGCCTCGAGCAGACCAACTCGTACGACCTCGTCCCGGCTGGCACGGACGCC
```

FIG. 2(D)

```
        1810      1820      1830      1840      1850      1860
TTCTCCTTCGCCGCCGGCACCGTCGTCGAGGTCCCTCTCGTCGACGTCGCTCTCGCTCGCC
        1870      1880      1890      1900      1910      1920
GCCGTCAACGCCTGGAAGGTCGGCCGCCGAGTCGGCCATCTCGCTCACCCGCCAAGTC
        1930      1940      1950      1960      1970      1980
CGCGAGACCTTTCTGGTCCGCCGGTCGACCTCGTCGCCGGCTCTCGTACCTCTCGCCG
        1990      2000      2010      2020      2030      2040
CGCACTCAGATCCCTCTACGCCTTCGTCCGCGAGGAGCTTGGCGTCAAGGCCCGCGGA
        2050      2060      2070      2080      2090      2100
GACGTCTTCCTCGGCAAGAGGTGACGATCGGCTCGAACGTCTCCAAGATCTACGAG
        2110      2120      2130      2140      2150
GCCATCAAGTCGGGATCAACAACGTCCCTCCTGCTTAGACACTCTTC
CCACTCTCGCATCCCCTATCCCGCCCTGCACTCTTAGGACTCGCTTCTTGTC
GGACTCGGATCTCGCATCGCTTCTTCGTTCTTCGGCTGCCCTCTCTAGACCGTGTCGGTAT
TACCTCGAGATTGTGAATACAAGCAGTACCCATCCAAAAAAAAAAAAA
```

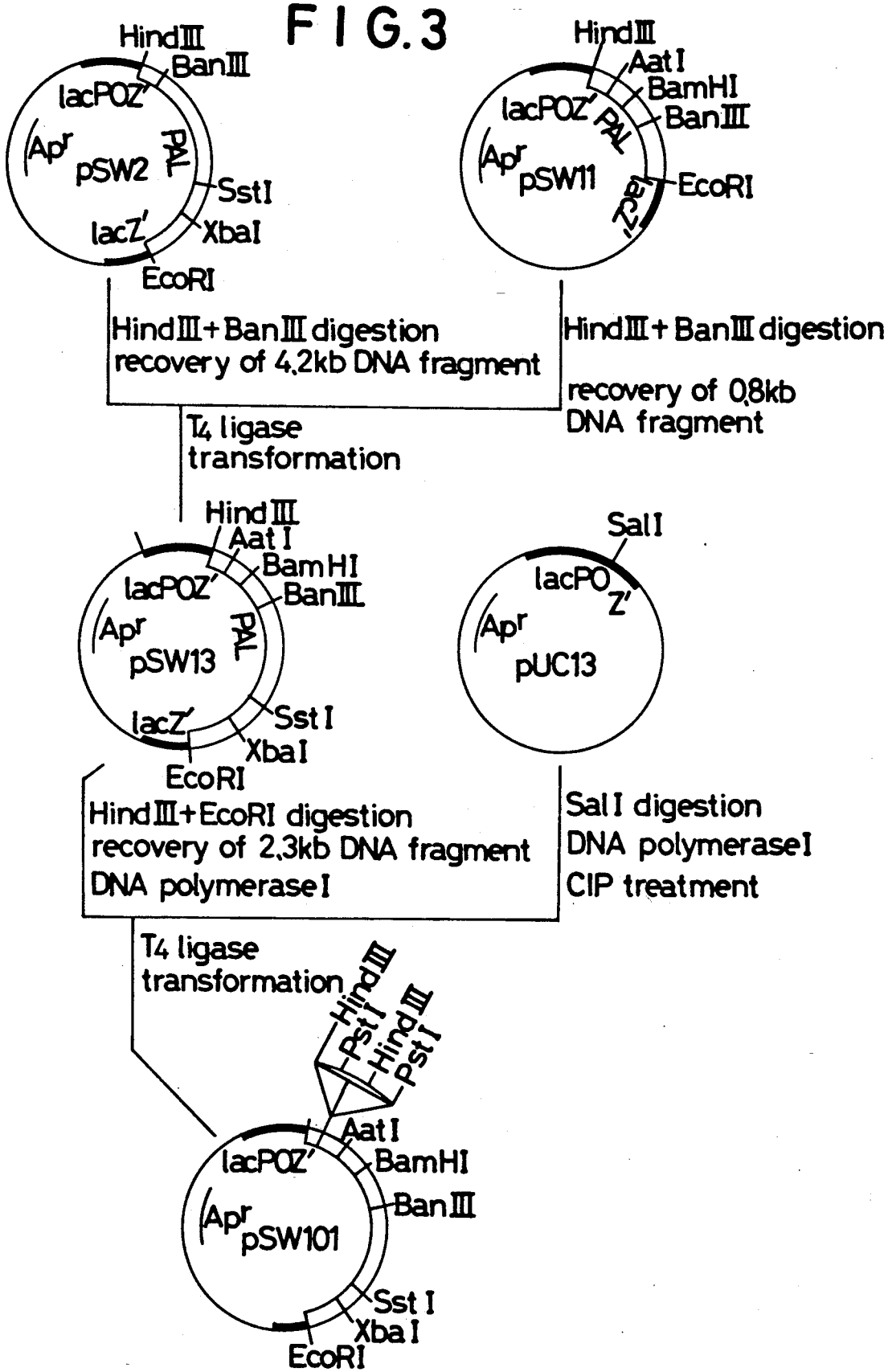

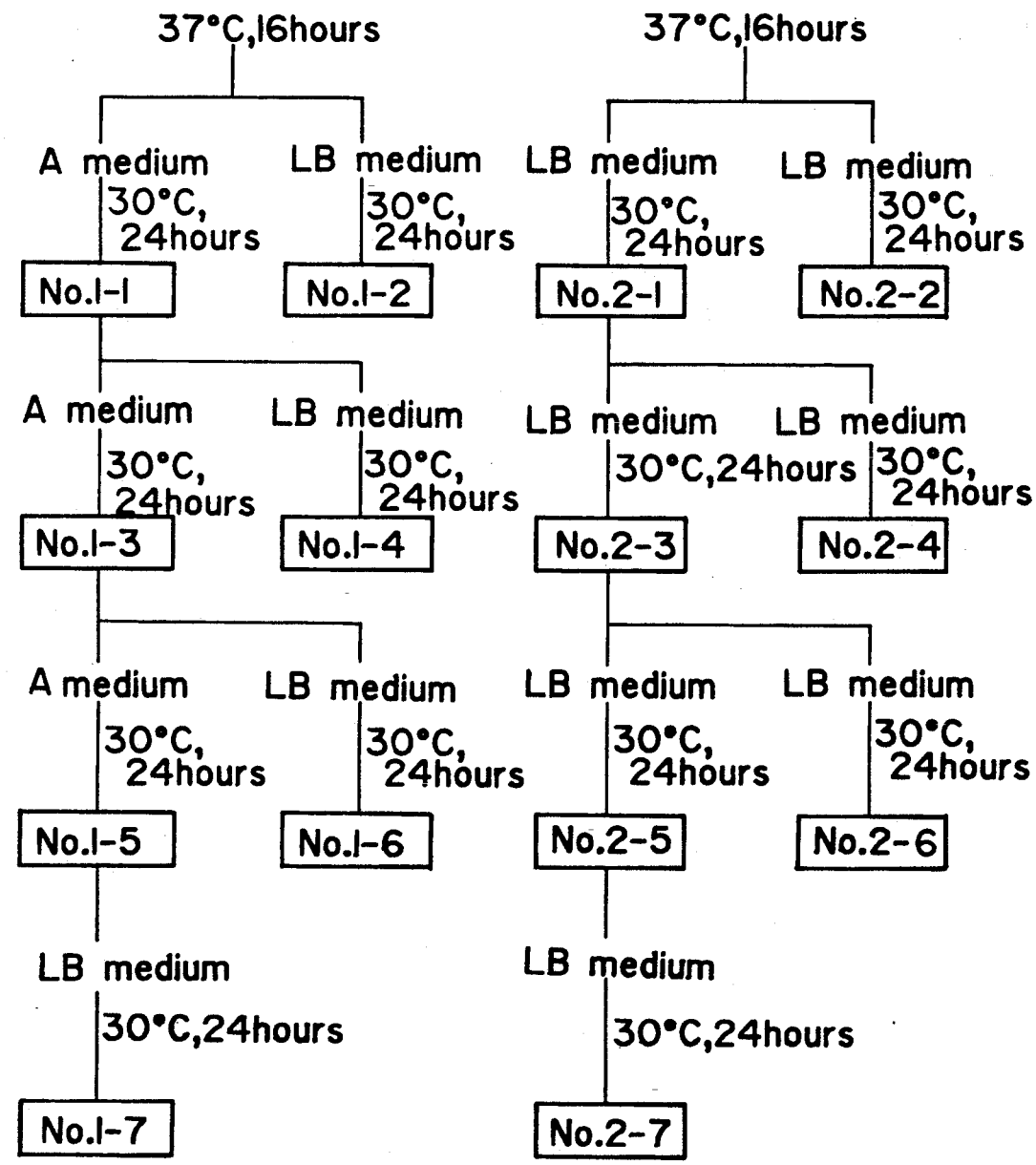

METHOD OF REGULATING EXPRESSION OF A FOREIGN GENE BY CONTROLLING THE SUGAR CONCENTRATION IN A MEDIUM AND A PROCESS OF PRODUCING A FOREIGN PRODUCT THEREBY

This is a continuation of application Ser. No. 07/156,586, filed Feb. 17, 1988, now abandoned.

BACKGROUND OF THE INVENTION

1. Field of the Invention

This invention relates to a useful method of regulating expression of a desired foreign gene, in which *Escherichia coli* carrying a recombinant plasmid (hybrid plasmid) with an insertion of said foreign gene therein grows efficiently whereas the expression of said foreign gene is efficiently suppressed. This invention also relates to a process of producing a foreign gene product by using said regulating method in which the period of the growth of *E. coli* carrying the hybrid plasmid therein is separated from the period of the expression of the foreign gene.

2. Description of the Prior Art

Currently, in virtue of the progress of gene recombination technology, a method has been developed for producing a desired foreign polypeptide in a host bacterium, in which a hybrid plasmid is constructed by inserting a structure gene, which originates from the animals, plants or microorganisms and encodes for the desired foreign polypeptide, into an expression vector which permits the expression of the foreign gene in the host bacterium and then the host bacterium is cultured to produce the desired foreign gene product in large amounts.

This technology has almost established the measures for producing useful substances, such as human insulin and human growth hormones.

As host bacteria for producing products of the foreign genes in such gene recombination technology, strains of *Escherichia coli* are widely used because their biological characteristics have been sufficiently investigated and, further they have no known pathogenicity and can easily grow in culture media having relatively simple compositions.

In general, however, the stability of the hybrid plasmid incorporated into *E. coli* spp. is not necessarily high so that deletion of the hybrid plasmid from *E. coli* or change in construction of the hybrid plasmid occurs during the period of cell growth, which results in high incidence of hybrid-plasmid-deleted cells bearing no capability in expressing foreign genes.

For example, in the industrial scale production, where mass culture is to be carried out, relatively long incubation time is generally required even in the preliminary culture to obtain a sufficient number of bacterial cells with high activity for the use in the following main bulk culture. Thus, high incidence of the deletion of hybrid plasmids from the bacterial cells as mentioned above can not be avoided. In consequence, the number of the effective foreign genes in the culture decreases as the number of the hybrid-plasmid-deleted cells increases, which results in a poor yield of the desired foreign gene product in the final culture.

In addition, cells can not efficiently grow in a usual culture accompanied with a foreign gene expression.

In view of the aforementioned problem caused by the use of the hybrid plasmid in the culture, the method of separating the period of cell growth from that of gene expression has been brought into discussion.

More precisely, the method comprises culturing a host bacterium carrying a hybrid plasmid with an insertion of a foreign gene therein under the conditions such that the expression of the foreign gene in the hybrid plasmid is suppressed until a desired number of cells be obtained and thereafter the suppression be released to permit the expression of the foreign gene and the culture be continued. In consequence, the incidence of hybrid-plasmid-deleted cells is suppressed as low as possible so that the foreign gene product are efficiently produced.

A known example of the method of controlling expression of a foreign gene as such comprises the use of an inducible-type expression promoter as the hybrid plasmid so that the expression of the foreign gene can voluntarily induced by addition of an inducer which inactivates repressors such as the $P_L$lambda promoter/operator of the *E. coli* lambda phage or the trp-promoter/operator of the *E. coli* tryptophan operon.

Another known example of the method of controlling expression of a foreign gene comprises the use of a temperature-dependent-type vector which has a temperature-dependent replication origin (i.e., the vector starts replication only at a certain range of specified temperatures) and thus the foreign gene expression is regulated by changing the culture temperature.

However, in the case of using the inducible-type expression promoter, the production cost tends to be high since the expression inducers are expensive and furthermore, the incidence of the hybrid-plasmid-deleted bacteria cannot be sufficiently prevented. Consequently, the method cannot be applicable to the industrial scale culture.

Furthermore, in the case of using the temperature-dependent-type vector, the incidence of the hybrid-plasmid-deleted bacteria cannot be prevented effectively and additionally, complicated apparatus for temperature control is required.

SUMMARY OF THE INVENTION

In view of the above-mentioned problems and in quest of establishing more effective means to produce foreign gene products, the present inventors have made several investigations in terms of fermentation technology with regards to the characteristics of *E. coli* carrying hybrid plasmids therein. In the course of the investigations, it was found out that expression of a foreign gene in *E. coli* carrying a hybrid plasmid with the foreign gene inserted therein was effectively controlled by regulating a concentration of sugar component such as glucose which is readily metabolized and utilized as a carbon source in a culture medium for *E. coli*.

Furthermore, the present invention was based on the conclusion that in the production of a foreign gene product by culturing bacteria carrying the hybrid plasmid introduced therein, it is possible to obtain the sufficient bacterial mass containing reduced number of hybrid-plasmid-deleted cells and thereafter to produce the sufficient quantities of the foreign gene product as such by means of changing sugar concentration of the culture medium for these two periods so as to separate the period of the bacterial growth process from that of the foreign gene expression process.

One objective of the present invention is to provide a simple and effective method of controlling expression of a desired foreign gene inserted into a hybrid plasmid in the culture of *E. coli* carrying the hybrid plasmid introduced therein.

Another objective of the present invention is to provide an appropriate method of effectively producing a desired foreign gene product in high concentration in the culture, particularly, for producing a foreign gene product on an industrial scale by using *E. coli* carrying a hybrid plasmid with an insertion of the foreign gene therein.

A method of regulating expression according to the present invention to achieve the above-mentioned objectives comprises a process of maintaining the concentration of a sugar as a carbon source in the culture for *E. coli* at 0.3% or more so as to suppress expression of a desired foreign gene in *E. coli* which carries the hybrid plasmid having been constructed by insertion of the desired foreign gene into an expression vector.

Thus, in a method of controlling expression according to the present invention, the expression of a foreign gene in a hybrid plasmid introduced into *E. coli* is effectively controlled by such a simple means as to control the sugar concentration in a medium.

Furthermore, in applying a method according to the present invention to the production of a foreign gene product, sufficient bacterial cell growth and, at the same time, low incidence of the deletion of the hybrid plasmid from the bacterium can be achieved by distinctly separating the period of the cell growth process from that of the foreign gene expression process to efficiently proceed with those processes. As a result, by using this method, the product corresponding to the desired foreign gene is produced in the culture in high concentration so that efficient production of the foreign gene product can be achieved.

In accordance with the present invention, there is no need to use expensive inducers as required in the conventional method by using inducible-type plasmids and in addition, there is no need for such a specific apparatus as required in the aforementioned temperature controlling system, since the control of the expression of the foreign gene can be accomplished by such a simple method as manipulating the sugar concentration in a medium.

Furthermore, according to the present invention, the industrial scale mass culture for producing a foreign gene product can be easily facilitated because the incidence of hybrid-plasmid-deleted bacteria can be effectively suppressed.

BRIEF DESCRIPTION OF THE DRAWINGS

FIG. 2, consisting of (A)-(D), illustrates the nucleotide sequence of DNA including the regions encoding for PAL, the DNA having been cloned as described in Reference Example 1.

FIG. 3 is a flowchart showing the steps in process of constructing pSW101.

FIGS. 13 and 14 are flowcharts showing the procedures and culture conditions used in Example 5 and Comparative Example 1, respectively.

DETAILED DESCRIPTION OF THE INVENTION

Figure 1:
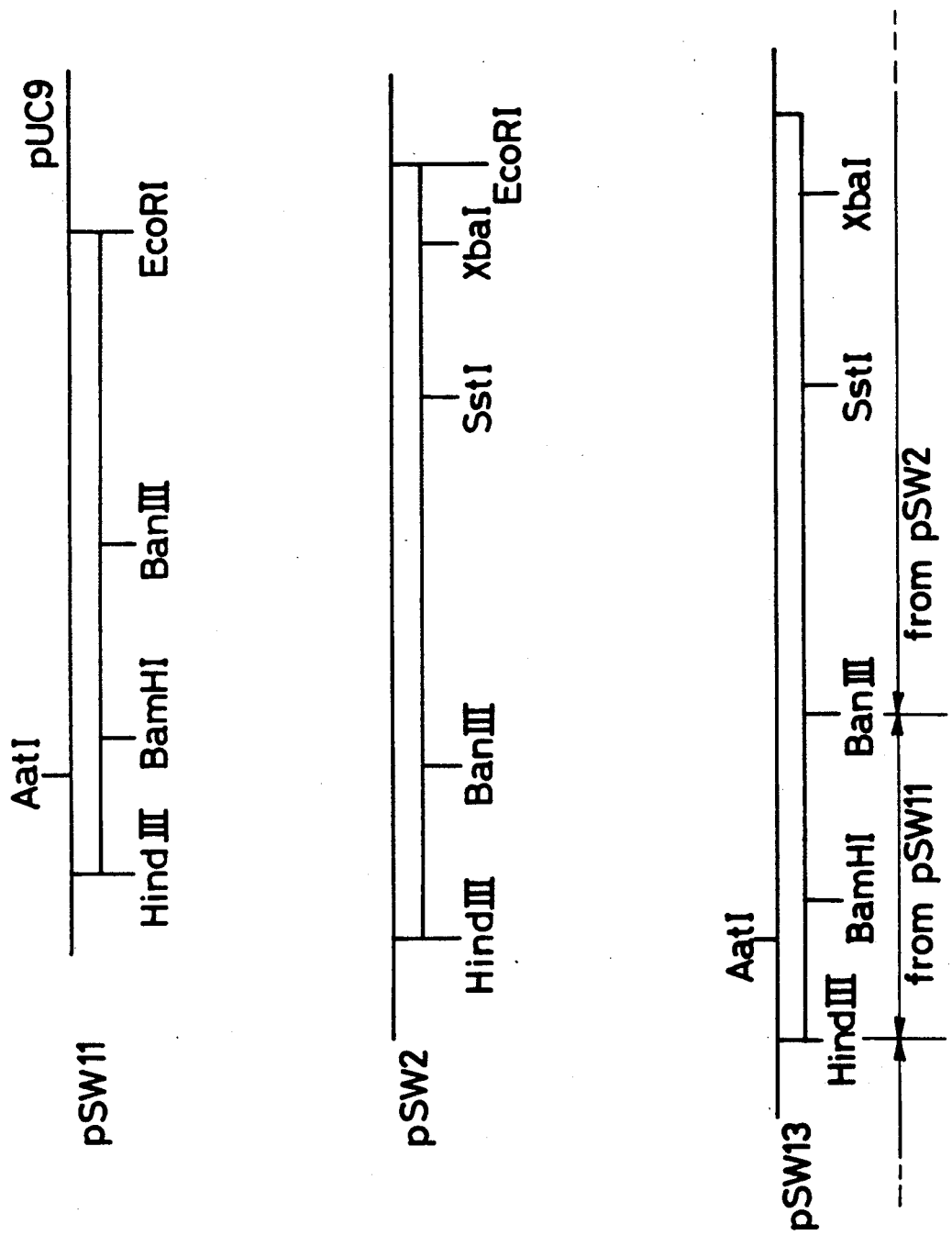
FIG. 1 illustrates restriction enzyme cleavage maps of the regions related to the structure gene for phenylalanine ammonialyase (PAL) in pSW11, pSW2 and pSW13.

A hybrid plasmid (recombinant plasmid) as used in the present invention is that obtained by insertion of a desired foreign gene into an expression vector which has a construction to permit expression of the foreign gene in *E. coli*.

An example of the expression vector consisting the hybrid plasmid comprises a vector which can replicate in *E. coli* and a promoter linked to the vector, the promoter being selected from a varieties of promoters such as the P$_L$ promoter of the lambda phage (the P$_L$ lambda promoter); the promoter of the tryptophan operon (the trp promoter); and a combined promoter comprising the P$_L$ lambda promoter and the tac promoter composed of the trp promoter minus 35 region and the lac UV-5 promoter minus 10 region.

An example of the foreign gene as used in the present invention is a structural gene encoding for a polypeptide which is not usually produced by a wild type strain of *E. coli*, such as a polypeptide of non-*E. coli* origin having substantially the same amino acid sequence as that derived from a eukaryotic cell.

A method of regulating expression according to the present invention comprises controlling a concentration of a sugar component which is readily metabolized and utilized as a carbon source, such as glucose, fructose, mannose, maltose or sorbitol, in a culture medium for *E. coli* carrying a hybird plasmid incorporated therein, thereby expression of a foreign gene having been inserted into the hybrid plasmid be regulated.

More specifically, in order to suppress expression of the foreign gene, the concentration of a sugar component in the medium for culturing *E. coli* carrying the hybrid plasmid therein is to be maintained at 0.3% or more, whereas it is to be maintained at less than 0.3% in order to allow the foreign gene to be highly expressed.

When a bacterium carrying an incorporated hybrid plasmid therein is cultured in a medium in which the sugar concentration is maintained at 0.3% or more, the expression of a foreign gene in the hybrid plasmid can be effectively suppressed and the bacterium grows well and furthermore, incidence of hybrid-plasmid-deleted bacteria in the culture is effectively suppressed during the culture until a desired number of cells are obtained.

In addition, a method according to the present invention permits controlling the expression of a foreign gene by such a simple means as to control the sugar concentration in a medium so that there is no need to use specifically expensive reagents such as expression inducers as described above. Furthermore, additional facilities for temperature control is not required.

A foreign gene product derived from the foreign gene can be efficiently produced by using a method of the present invention in which *E. coli* carrying a hybrid plasmid with an insertion of the foreign gene therein is cultured under the specified conditions, thereby controlling the gene expression so as to effectively produce the foreign gene product.

More specifically, a method of regulating expression according to the present invention for producing a foreign gene product in *E. coli* carrying an incorporated hybrid plasmid therein comprises:

a) a first culture process in which *E. coli* carrying the hybrid plasmid incorporated therein is cultured in a medium with a sugar component at a concentration maintained at 0.3% or more and b) a second culture process in which *E. coli* grown in the first culture process is cultured in a medium with the sugar component at a concentration maintained at less than 0.3%.

In the first culture process according to the present invention, the sugar concentration in the medium is maintained at 0.3% or more so as to suppress the expression of the foreign gene which is present in the hybrid plasmid having been incorporated into *E. coli*. In consequence, *E. coli* grows sufficiently to give a desired number of cells in the culture of the first culture process. Furthermore, the incidence of the hybrid-plasmid-deleted cells is suppressed to the extent almost negligible during the period of cell growth. Furthermore, in the case of subculture for maintaining cell activity over a long period of time, the incidence of the hybrid-plasmid-deleted cells can be similarly suppressed by this method of controlling the foreign gene expression.

In the second culture process according to the present invention, the sugar concentration in the medium is to be maintained at less than 0.3% so as to release the suppression of the foreign gene expression in the bacterial cell carrying the hybrid plasmid therein. Consequently, the foreign gene is highly expressed in the cell carrying the hybrid plasmid, thereby permitting the effective production of the foreign gene product. In this process, the number of hybrid-plasmid-deleted cells is almost negligible among the cells having been obtained during the first culture process so that the foreign genes in almost all the cells in the culture are to be expressed efficiently, thereby permitting the production of the foreign gene product in sufficiently high concentration.

An example of the ranges of the sugar concentrations to be used in combination is 0.3-1.0% for the first culture process and less than 0.3% for the second culture process.

According to the present invention thus described, the yield of the foreign gene product can be geometrically increased since the foreign gene product is produced in high concentration when a large number of cells are cultured to obtain mass culture.

Furthermore, a method according to the present invention is applicable to the culture of prolonged period of time as required in the first culture process, whereas the aforementioned conventional method, in which cell growth is associated with the foreign gene expression, is not applicable to the culture of long period of time because the rate of the hybrid-plasmid-deleted cells increases with extension of subculture time. Accordingly, a method according to the present invention is specifically suitable for the industrial mass culture where relatively long culture time is required for the preliminary culture.

The time to switch from the first culture process to the second culture process can be voluntarily selected as desired. It may, however, depend on the kind of bacterium carrying the hybrid plasmid therein or on the culture method to be used for these culture processes.

For example, when a method of the present invention is to be applied in the preliminary culture to obtain a small number of seed bacteria, followed by the batch system mass culture to obtain the main culture, the first culture process may be adopted in the preliminary culture and in the first half of log phase of the main culture and then the second culture process may be adopted in the culture thereafter.

A method according to the present invention will be more specifically understood from the following Reference Examples, Examples and Comparative Examples with the use of phenylalanine ammonialyase (hereinafter referred to as PAL).

REFERENCE EXAMPLE 1

(1) Isolation and Purification of mRNA for PAL

*Rhodosporidium toruloides* IFO 559 (also identified as ATCC 10788) was grown at 27° C. under aerated and agitated conditions in a synthetic medium (Table 1) containing 2% glucose. Immediately after depletion of the glucose in the culture, the cells were collected by centrifugation. The cells were washed with a sterile 0.85% sodium chloride solution and collected again by centrifugation to obtain washed wet cells.

TABLE 1

| | grams/l | | micrograms/l |
|---|---|---|---|
| Glucose | 20 | Biotin | 2 |
| (NH4)2SO4 | 3 | Calcium pantothenate | 400 |
| KH2PO4 | 1 | Inositol | 2000 |
| MgSO4.7H2O | 0.5 | Niacin | 400 |
| NaCl | 0.1 | p-Aminobenzoic acid | 200 |
| CaCl2 | 0.1 | Pyridoxine hydrochloride | 400 |
| | | Riboflavin | 200 |
| | | Thiamine hydrochloride | 400 |

These washed wet cells were readily suspended in a PAL induction medium [i.e., 0.17% Yeast Nitrogen Base w/o Amino Acid and Ammonium Sulfate (Difco Laboratories) supplemented with 2% L-phenylalanine] to give a cell concentration of 0.5-0.8%, and the resultant suspension was incubated for the induction of PAL at 27° C. for 2 hours with shaking. After the induction, the cells were recovered by centrifugation. The collected wet cells were suspended in an equal volume of sterile water, and the resultant suspension was dropped into liquid nitrogen to obtain frozen cells.

Ten grams of the frozen cells having been treated for the PAL induction for 2 hours as described above was added to liquid nitrogen in a mortar and finely ground with a pestle. The liquid nitrogen evaporated spontaneously. As soon as the frozen ground material began to thaw, 50 ml of buffer solution "C" [composed of 0.1M Na2HPO4 (pH 7.4), 0.15M sodium chloride, 1% sodium deoxycholate and 1% Triton X-100 (registered trademark, Rohm & Haas, USA)] supplemented with 5% sodium dodecylsulfate (SDS) were added thereto. The resultant mixture was gently stirred for 30 minutes for thorough mixing.

After completion of the mixing, 50 ml of a phenol-chloroform mixture (composed of phenol, chloroform and isoamyl alcohol in a volume ratio of 25:24:1) was added thereto and mixed therewith by stirring for 15 minutes.

The resultant mixture was centrifuged to recover the aqueous layer. To this aqueous layer was added 50 ml of the phenol-chloroform mixture, followed by stirring for 15 minutes. The resultant mixture was then centrifuged again to recover the aqueous layer. This extraction procedure with the phenol-chloroform mixture was repeated twice more.

To the finally obtained aqueous layer was added 5M NaCl so as to give a final sodium chloride concentration of 0.2M. Then, 2.5 volumes of cold ethanol was add thereto. The resultant mixture was stored at or below −20° C. to precipitate nucleic acid components.

The precipitate so formed was collected by centrifugation, washed with cold ethanol and then dried under reduced pressure.

The dry material thus obtained was dissolved in 10 ml of sterile water, and the resultant solution was heated at 65° C. for 5 minutes. Thereafter, a mRNA component was isolated according to the method of Maniatis using oligo-d(T) cellulose [Maniatis, T., et al., "Molecular Cloning" (1982)].

The mRNA component thus obtained was dissolved in a sample buffer solution (composed of 5M urea, 1 mM EDTA and 0.05% bromophenol blue) and then heated at 65° C. for 2 minutes to destroy the higher-order structure of mRNA. Thereafter, using an 8M urea-acrylamide slab gel (having an acrylamide concentration of 3% and containing 8M urea), the mRNA component was electrophoresed at 100 volts for 1.5 hours in an electrophoresis buffer solution (composed of 89 mM Tris, 89 mM boric acid and 2 mM EDTA).

After completion of the electrophoresis, the acrylamide gel was treated with ethidium bromide and mRNA bands were visualized under ultraviolet light. A gel portion supposedly including mRNAs ranging from 2.0 to 3.0 kb in size was divided into three equal parts in the lengthwise direction, and gel segments of the three parts were cut out of the slab gel.

Each gel segment was sealed into a dialysis tube, which was immersed in an electrophoresis buffer solution having the aforesaid composition. Thus, mRNAs were electrically eluted from the gel segments.

To the liquid inside the individual dialysis tube was added the phenol-chloroform mixture for the extraction of mRNA. The extraction procedure was repeated two times. The aqueous layer thus obtained was further treated with ether to remove residual phenol. To this finally obtained aqueous layer were added a 1/10 volume of a 3M aqueous solution of sodium acetate (pH 5.2) and then 2.5 volumes of cold ethanol. The mixture thus obtained from each of the gel segments was stored at −20° C. to precipitate mRNA.

In order to test for the presence of the mRNA for PAL in the mRNA preparation extracted from each of the three gel segment, mRNA in the preparation was translated into proteins and the proteins thus produced were tested with an antibody specific to PAL.

More specifically, individual mRNA was subjected to the translation with a cell-free translation kit using the lysate of rabbit reticulocytes [Pelham, H. R., et al., European J. Biochem., 67, 247–256 (1976)].

The rabbit reticulocyte assay kit used was a product of Promega Biotec Co. and the labeled amino acid used was $^{35}$S-methionine (Amersham Co.).

Identification of PAL in the proteins synthesized in vitro was carried out by the translation of the mRNA in the rabbit reticulocyte translation system as follows:

To dissolve the proteins having been produced by the translation, buffer solution "C" was added to the translation reaction mixture. After removal of insoluble substances by centrifugation, anti-PAL rabbit IgG (laboratory-made) was added to the reaction mixture. The reaction mixture was then allowed to stand on ice for 30 minutes. Subsequently, anti-rabbit IgG sheep serum (laboratory-made) was added to the reaction mixture. The mixture was allowed to stand on ice for 30 minutes to precipitate proteins together with the rabbit antibody component. The precipitate was recovered by centrifugation, washed twice with buffer solution "C" and then dissolved in a combined solution of a mixed solution of 2% SDS and 10% beta-mercaptoethanol with another mixed solution of 0.1M Tris-phosphate (pH 6.8), 1% SDS and 50% glycerol, in a volume ratio of 3:1. The resultant reaction mixture was heated at 95° C. for 2 hours to cleave disulfide bridges in the protein molecules. The solution was then subjected to SDS-polyacrylamide slab gel electrophoresis (at an acrylamide concentration of 10%) according to the method of Laemmli [Laemmli, U. K., Nature, 227 680–685 (1970)]. After completion of the electrophoresis, the gel was dried and the presence of PAL was detected by autoradiography.

Each of the mRNA fractions derived from the gel fragments was tested according to the procedure described above. Thus, the fraction containing the mRNA coding for PAL was identified.

(2) Synthesis of Double-stranded cDNA (ds-cDNA) for PAL by Using mRNA for PAL

The mRNA coding for PAL was purified from the gel segment obtained after electrophoresis of the mRNA fractions derived from the cells having been subjected to the treatment for the PAL induction for 2 hours as described above in Section (1). The mRNA thus obtained was treated with AMV reverse transcriptase for the synthesis of the single-stranded cDNA-transcript molecule of the mRNA for PAL [Gugger, U., et al., Gene, 25, 263–269 (1983)].

More specifically, cDNA-mRNA hybrid was first synthesized, consequently, mRNA was removed by treatment with RNase H and then the double-stranded cDNA (ds-cDNA) was constructed by treatment with DNA polymerase I and T4 DNA ligase.

(3) Construction of ds-cDNA Having oligo-dC Tails at 3′-Termini

The ds-cDNA obtained in Section (2) above was treated with terminal deoxynucleotidyltransferase (TdT) to add oligo-dC tails to 3′-termini of the ds-cDNA.

More specifically, 3 micrograms of the ds-cDNA was dissolved in a TdT reaction buffer solution [composed of 100 mM potassium cacodylate (pH 7.2), 2 mM cobalt chloride and 0.2 mM dithiothreitol and supplemented with 0.2 mM dCTP]. After preheating of the buffer solution at 37° C. for 5 minutes, 50 units of TdT was added and the resultant reaction mixture was incubated at 37° C. for 15 minutes so as to allow the reaction to proceed. Thereafter, EDTA was added to a final concentration of 40 mM, subsequently the reaction mixture was placed on ice and the phenol-chloroform mixture was added to the reaction mixture to denature and inactivate the TdT. The reaction mixture was centrifuged to remove denatured insoluble proteins therein and the supernatant thus obtained was subjected to a phenol extraction. The aqueous layer was taken and mixed with cold ethanol. The precipitate so formed was collected, washed with 70% ethanol, and then dried under reduced pressure to obtain the ds-cDNA having oligo-dC tails at the 3′-termini.

(4) Construction of Hybrid Plasmid

Joint of Plasmid pUC9 Having Oligo-dG Tails to ds-cDNA Having Oligo-dC Tails

The ds-cDNA with oligo-dC tails obtained in Section (3) was joined to the plasmid pUC9 with oligo-dG tails (readily available from Pharmacia Co., Sweden) according to the method of Maniatis, known as the dC-dG homopolymer method.

(5) Transformation and Clone Selection

The hybrid plasmid obtained in Section (4) above, consisting of the oligo-dG tailed pUC9 and the oligo-dC tailed ds-cDNA, was introduced into $CaCl_2$-treated *Escherichia coli* (MC-1061) [Casadaban, M. T., et al., Method in Enzymology, Vol. 100, 293–308, Academic Press, New York (1983)] according to the competent cell method.

From about 40,000 colonies obtained in the manner described above, transformed cells were selected according to the colony hybridization method based on the procedure of Grunstein et al. [Grunstein, M., et al., Proc. Natl. Acad. Sci., USA., 72, 3961 (1971)].

The probe DNA used in the colony hybridization was the $^{32}$P-labeled single-stranded cDNA obtained in the same manner as described above in Section (2), except that alpha-$^{32}$P-dCTP was added to the reaction mixture in place of unlabeled dCTP.

From the positive colonies thus obtained, plasmids were extracted and purified. The plasmids were digested with various restriction endonucleases, and the resultant DNA fragments were analyzed by agarose gel electrophoresis.

(6) Construction of ds-cDNA Containing Complete Structure Gene Coding for PAL Plasmids pSW2 and pSW11 were isolated from the transformants obtained in Section (5) above.

Moreover, as a result of the analysis carried out in Section (5) above by using various restriction endonucleases, it was found out that the complete cDNA having the full length corresponding to the mRNA for PAL could be constructed by combining pSW2 with pSW11. Thus, these two plasmids were individually extracted and purified from the transformants carrying them. The plasmid obtained from the cell carrying pSW2 was digested with the restriction endonuclease BanIII, and then with the restriction endonuclease HindIII. The resultant fragment mixture was fractionated by agarose gel electrophoresis. Thus, a DNA fragment having a size of 4.2 kb was recovered and purified by subjecting several times to the procedure comprising treatment with the phenol-chloroform mixture and precipitation with cold ethanol.

Separately, the plasmid obtained from the cell carrying the pSW11 was digested with the restriction endonucleases BanIII and HindIII. By subjecting the resultant fragment mixture to electrophoresis, a DNA fragment having a size of 0.8 kb was recovered and purified.

The 4.2 kb and 0.8 kb DNA fragments thus obtained were circularized by using T4 DNA ligase, and the resultant product was used to transform *E. coli* (JM83, ATCC 35607) [Messing, J. and Vieira, J., Gene, 19, 259–268 (1982)].

Plasmids extracted from the transformants having been selected by virtue of their ampicillin resistance were treated with various restriction endonucleases to construct cleavage maps. Thus, plasmid pSW13 containing the full length DNA structure for PAL was obtained. The restriction endonuclease cleavage map for DNA coding for PAL are shown in FIGS. 1 and 3.

(7) Determination of Nucleotide Sequence of Cloned DNA

The cloned DNA from the plasmid pSW13 isolated from the cloned cell carrying the pSW13 was digested with various restriction endonucleases. Nucleotide sequences of the resultant restriction fragments were adequately analyzed by the method of Maxam-Gilbert (a chemical decomposition method) and also by biochemical means using the method of Maat (dideoxy method) [Maat, J., et al., Nucleic Acids Research, 5, 4537–4545 (1978)]. The nucleotide sequences thus obtained were edited by using the GENAS program produced by Mitsui Information Development Co. The DNA nucleotide sequence so determined is shown in FIG. 2, consisting of (A)–(D).

The structure gene coding for PAL including the initiator codon and the terminator codon comprises the nucleotide sequence extending from 1 to 2151.

(8) Construction of pSW101 (See FIG. 3)

In 14 microliters of a reaction medium [composed of 7 mM Tris-HCl (pH 7.5), 0.7 mM EDTA, 7 mM $MgCl_2$, 175 mM NaCl, 7 mM beta-mercaptoethanol and 0.01% bovine serum albumin (BSA), 0.9 micrograms of pUC13 (Pharmacia Co.)] was digested with 10 units of the restriction endonuclease SalI at 37° C. for 16 hours. After the digestion was accomplished, a linear pUC13 DNA fragment was obtained by the phenol-chloroform treatment and ethanol precipitation.

Subsequently, the linear DNA was treated with the Klenow fragment of DNA polymerase I (Takara Shuzo K. K.) in a nick-translation buffer solution [composed of 50 mM Tris-HCl (pH 7.5), 10 mM $MgCl_2$, 0.1 mM dithiothreitol, 2% BSA, 80 μM dATP, 80 μMdGTP, 80 μM dTTP and 80 μM dCTP] at room temperature for 30 minutes. Thus, cohesive ends of the linear DNA were converted to flush ends. After the proteins were removed with phenol, the DNA fragment was recovered by precipitation with cold ethanol. Subsequently, in order to prevent self-circularization of the resultant linear pUC13 DNA, the 5'-terminal phosphoryl groups thereof were removed by treatment with phosphodiesterase from calf spleen (CIP; Boehringer Mannheim).

Separately, the plasmid pSW13 was extracted and purified from the clone carrying the pSW13. The plasmid pSW13 was treated with the restriction endonuclease DraI in a reaction medium [composed of 4 mM Tris-HCl (pH 7.5), 0.4 mM EDTA and 50 mM NaCl] at 37° C. for 28 hours. After the addition of a NaCl solution to the medium to give a sodium chloride concentration of 100 mM, the plasmid pSW13 was further treated with the restriction endonucleases EcoRI and HindIII at 37° C. for 16 hours.

After completion of the treatment, the reaction mixture was subjected to agarose gel electrophoresis, and a DNA fragment having a size of 2.3 kb was recovered from the gel. This DNA fragment was then subjected three times to the procedure comprising extraction with phenol, treatment with a phenol-chloroform mixture, and precipitation with cold ethanol. Thus, there was obtained a cDNA fragment coding for PAL.

In the aforesaid nick translation buffer solution, the cDNA fragment was treated with the Klenow fragment of DNA polymerase I at room temperature for 45 minutes, and then subjected three times to a procedure comprising treatment with a phenol-chloroform mixture and precipitation with cold ethanol. Thus there was obtained a cDNA fragment having flush ends.

The flush-ended cDNA thus obtained and the flush-ended pUC13 fragment prepared as above were joined by using T4 DNA ligase to construct the circular plasmid pSW101.

Using this hybrid plasmid, transformation of E. coli (JM83) was carried out according to the known method. Colonies were selected by virtue of ampicillin resistance and tested for the PAL activity. Consequently, the strain (MT-10410, FERM BP-1710) having the plasmid pSW101 was obtained.

(9) Construction of pYtrp6 and E. coli Transformation Thereby

The plasmid pSW101 constructed in the manner described above in Section (8) was digested with the restriction endonucleases PstI and BamHI. After electrophoresis on agarose gel, a fraction containing DNA of 370 bp was recovered. This fraction was divided into two portions and one was digested with BanI and the other with BbeI.

After the digestion, each fraction was subjected to acrylamide gel electrophoresis and thus a DNA fragment having a size of 70 bp from the digest with the BanI and a DNA fragment having a size of 280 bp from the digest with the BbeI were recovered.

The 70 bp fragment was treated with DNA polymerase I to obtain flush ends and then joined with ClaI (BanIII) linkers by means of ligation with T4 DNA ligase.

Figure 5:
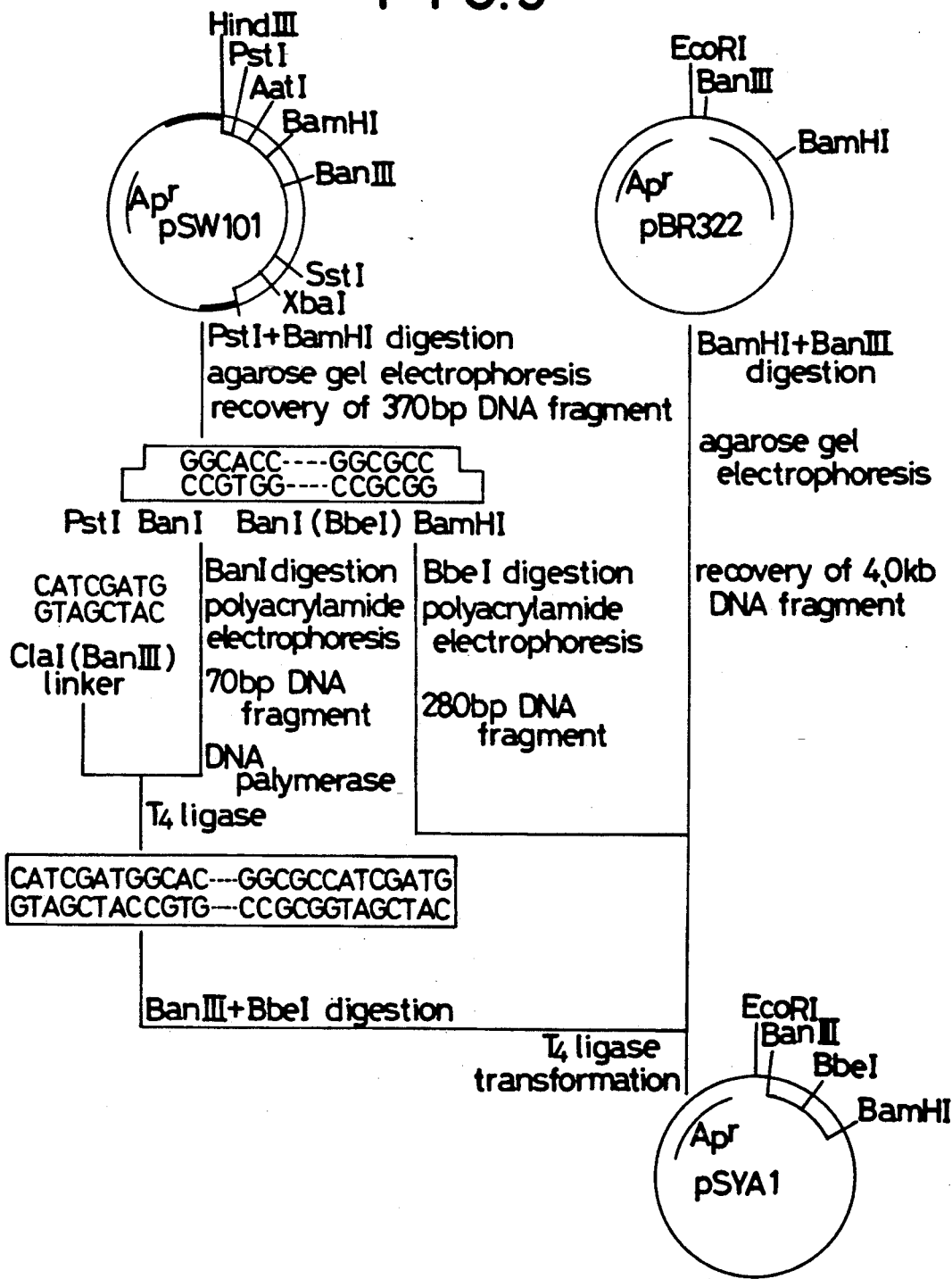
FIGS. 5-7 illustrate detailed partial views of the flowchart shown in FIG. 4.

The resultant DNA fragment having ClaI linkers at both ends thereof was digested with the restriction endonucleases BanIII and BbeI. Subsequently, as illustrated in FIG. 5, the resultant DNA fragment including ClaI linkers and the previously prepared BbeI fragment (280 bp) were joined by using T4 DNA ligase to the 4.0 kb fragment having been obtained by digesting pBR322 (Pharmacia Co.) with the restriction endonucleases BanIII and BamHI. The plasmid pSYA1 was thus constructed. Further, with use of the plasmid pSYA1, transformation of E. coli (MC-1061) was curried out according to the conventional calcium method. The E. coli cells carrying the pSYA1 were grown at 37° C. overnight in 3 ml of ampicillin-supplemented LB medium [composed of 10 g of Bacto-Tryptone (registered trademark, Difco Laboratories), 5 g of Bacto-Yeast Extract (registered trademark, Difco Laboratories), 5 g of NaCl, 1 g of glucose and 1 l of distilled water, the pH adjusted to 7.5 with NaOH]. The cells collected by centrifugation were suspended in 60 microliters of a solution composed of 50 mM glucose, 25 mM Tris-HCl (pH 8.0) and 10 mM EDTA. Then, 40 microliters of a 10 mg/ml lysozyme solution was added thereto and the resultant mixture was allowed to stand at room temperature for 5 minutes. After completion of the reaction, 200 microliters of 0.2N NaOH containing 1% SDS was added to the mixture. The reaction mixture was gently mixed by vortex, then placed on ice and allowed to stand thereon for 5 minutes. Then, 150 microliters of a 5M sodium acetate solution (pH 4.8) was added to the mixture. After gentle mixing with vortex, the mixture was placed on ice to terminate the reaction.

The resultant cell lysate was centrifuged at 12,000 rpm for 10 minutes to separate supernatant. The supernatant was then subjected three times to a procedure comprising the treatment with the phenol-chloroform mixture and precipitation with cold ethanol.

From the precipitate thus obtained, plasmid pSYA1 was extracted according to the conventional method. The plasmid pSYA1 was digested with the restriction endonucleases BamHI and BanIII and then a DNA fragment having a size of 350 bp was recovered.

Separately, the plasmid pSW13 constructed in Section (6) above was digested with the endonucleases XbaI and the resultant cohesive ends were treated with DNA polymerase I to produce flush ends. Subsequently, the HindIII linkers were joined to the pSW13 by means of ligation with T4 DNA ligase to construct plasmid pSW13H. The plasmid pSW13H was then digested with the restriction endonucleases BamHI and HindIII and a DNA fragment having a size of 1.9 kb was recovered after agarose gel electrophoresis.

Separately, the plasmid pVV1 [Nicols, B. P., and Yanofsky, C., Method in Enzymology, 101, 155 (1983)] containing a part of the trp operon of E. coli was digested with the restriction endonuclease HinfI.

After agarose gel electrophoresis, a DNA fragment having a size of 0.9 kb was obtained from the gel according to the method described above.

Cohesive ends of the 0.9 kb DNA fragment having been produced by digestion with the HinfI were converted to flush ends according to the procedure described in Section (8) above. The EcoRI linkers (GGAATTCC) were then joined to the 5'-flush ends of the DNA fragment by ligation with T4 DNA ligase.

The DNA fragment having the EcoRI linkers thus prepared was treated with the restriction endonuclease EcoRI to produce a DNA fragment having EcoRI-cleaved cohesive ends [Nicols, B. P. and Yanofsky, C., Method in Enzymology, 101, 155 (1983)].

Using T4 DNA ligase, the DNA fragment having the EcoRI cohesive ends was joined to the DNA fragment which had been obtained by treating the EcoRI-digested pBR322 with CIP according to the procedure described above in Section (8). The resultant product was then digested with the restriction endonucleases EcoRI and BglII. The digest was then subjected to agarose gel electrophoresis to obtain a DNA fragment having a size of 0.4 kb.

This 0.4 kb DNA fragment having three cleavage sites for the restriction endonuclease TaqI was partially digested with TaqI. A DNA fragment having a size of 345 bp was thus obtained.

This 345 bp DNA fragment was joined to the 4.3 kb DNA fragment obtained by digesting pBR322 with the restriction endonuclease EcoRI and ClaI. Thus, plasmid pFtrp2 containing the trp promoter was obtained.

Figure 6:
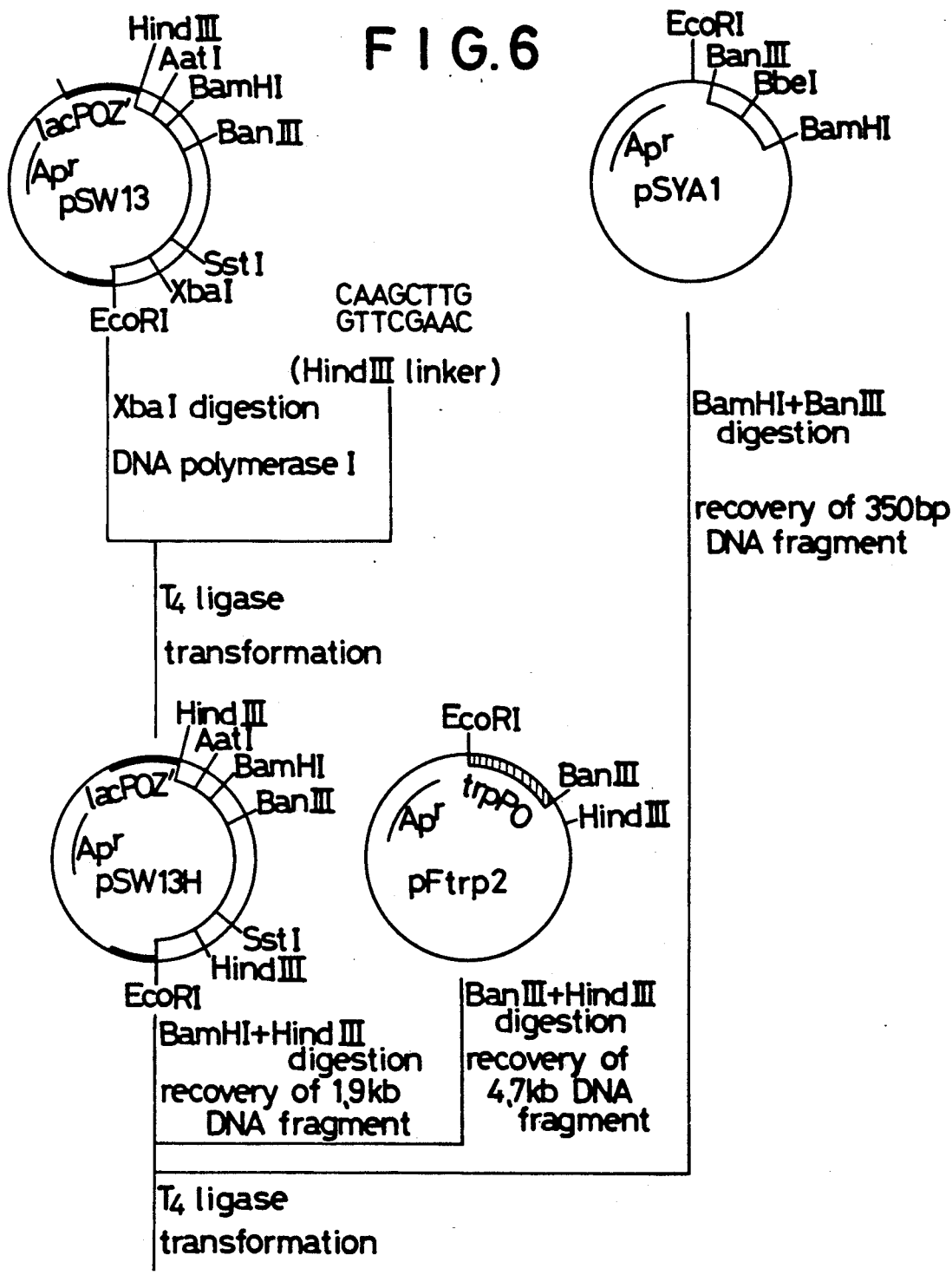

The plasmid pFtrp2 constructed in the manner as described above was digested with the restriction endonucleases BanIII and HindIII. After agarose gel electrophoresis, a fragment of 4.7 kb was obtained. As illustrated in FIG. 6, this fragment was then joined to the 350 bp BamHI-BanIII fragment and the 1.9 kb BamHI-HindIII fragment, both previously prepared, by ligation with T4 DNA ligase. The circular plasmid pSYA2 as shown in FIG. 7 was thus constructed.

Subsequently, the plasmid pSYA2 was partially digested with BanIII and the resultant cohesive ends thereof were treated with DNA polymerase I to produce a flush-ended fragment. This fragment was then circularized by ligation with T4 DNA ligase to construct plasmid pYtrp6 having a cleavage site for NruI (FIG. 7).

E. coli (MC-1061) was transformed with the plasmid pYtrp6 according to the conventional method. Cloned cells were selected by virtue of ampicillin resistance and were tested for the PAL activity. The transformed cell of E. coli exhibiting the PAL activity thus isolated was named MT-10414 (FERM BP-1712).

Figure 4:
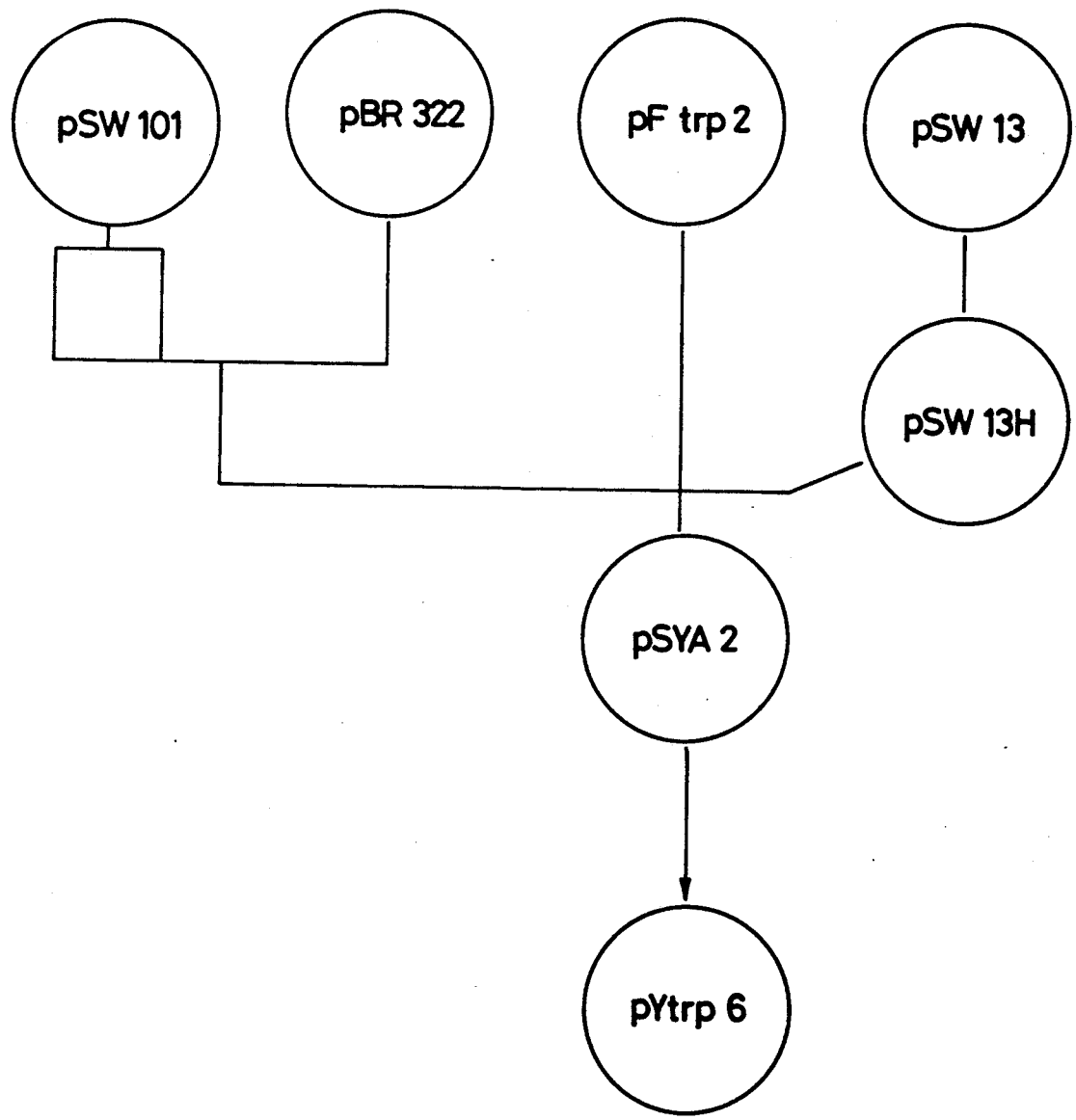
FIG. 4 is a flowchart showing the steps in process of constructing pYtrp6.
Figure 7:
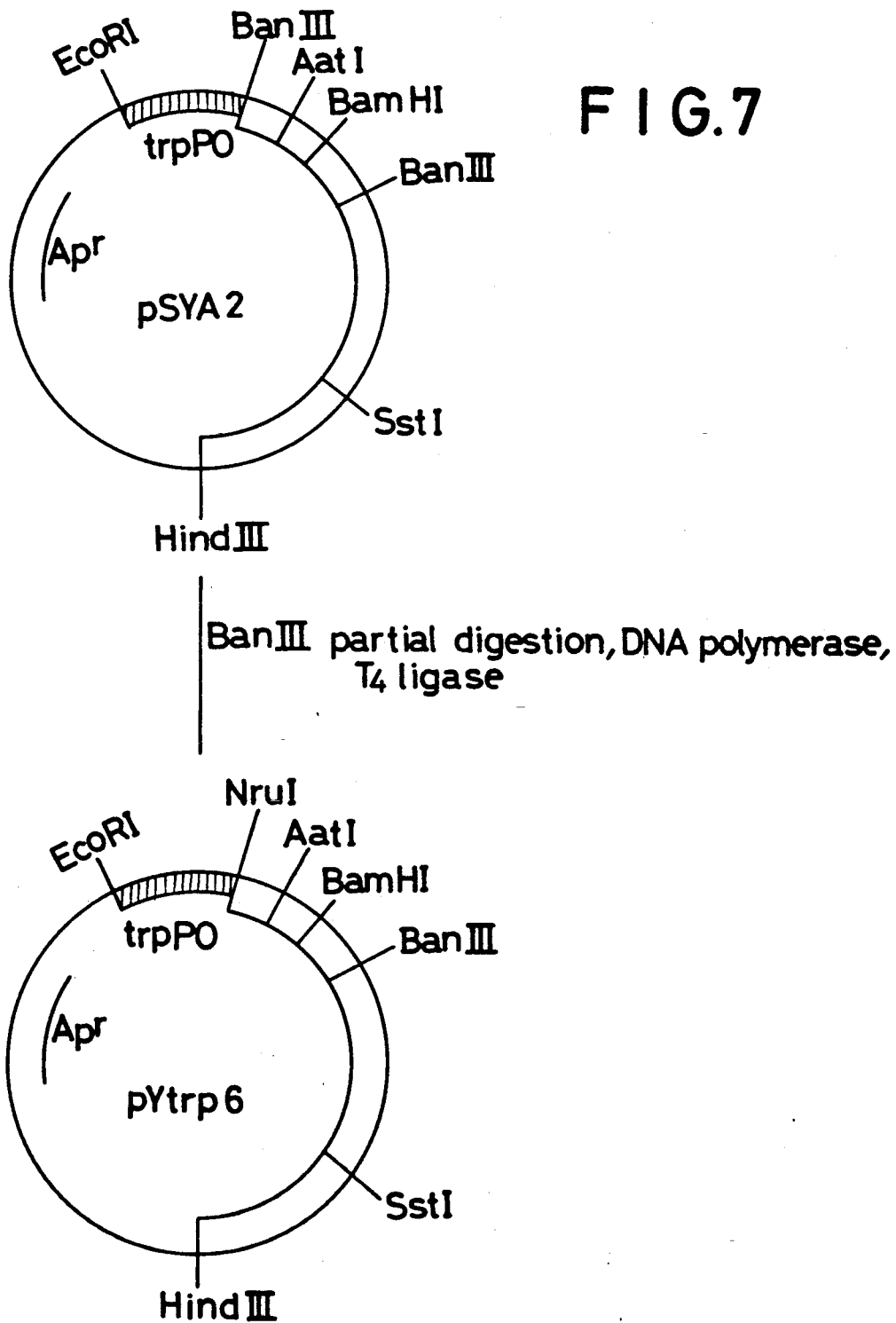

The steps of construction of the plasmid pYtrp6 is illustrated in outline in FIG. 4 and in detail in FIGS. 5, 6 and 7.

REFERENCE EXAMPLE 2

Construction of Plasmid pSW115

Figure 8:
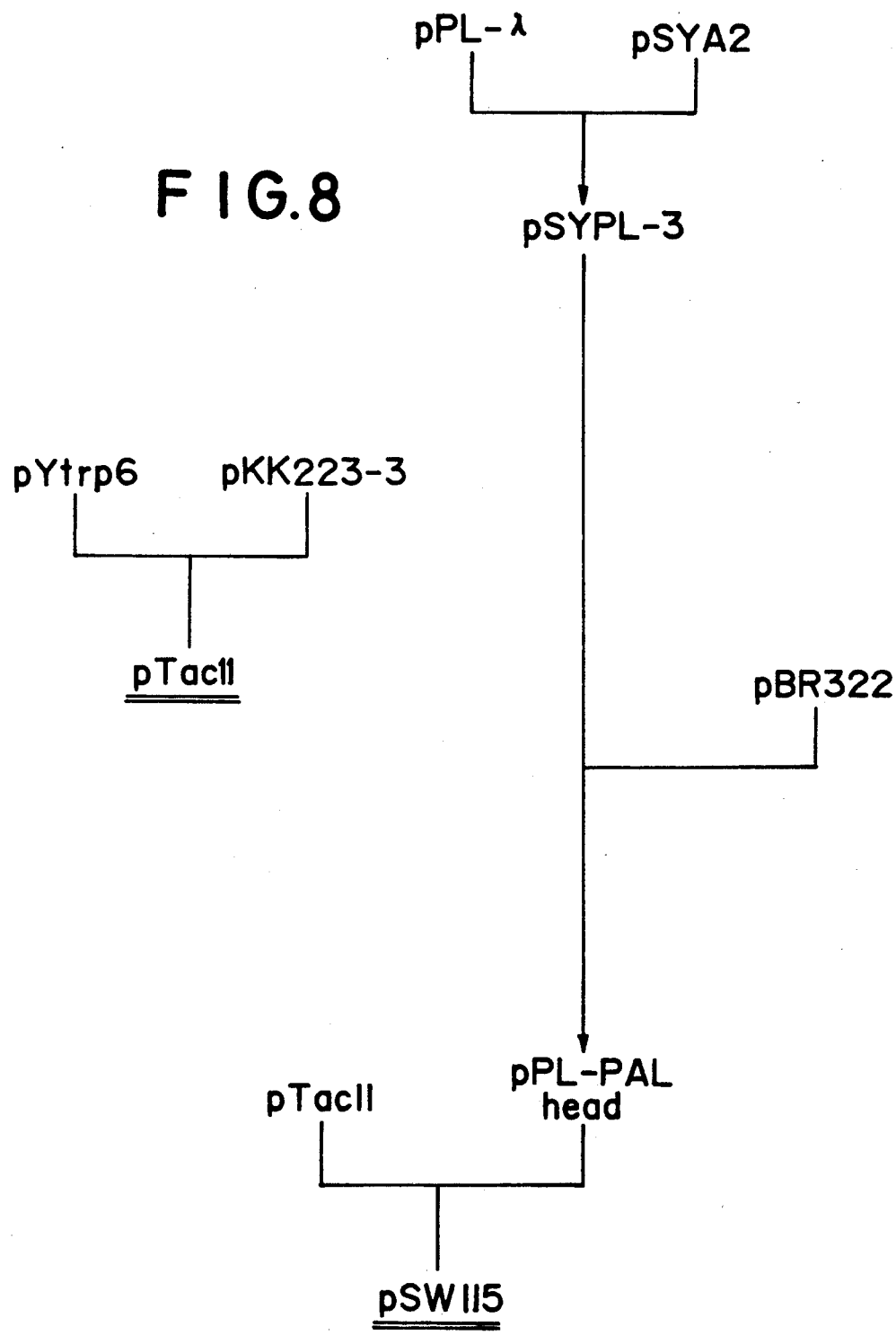
FIG. 8 illustrates schematic diagrams showing steps in process of constructing hybrid plasmids constructed in Reference Example 2.

The procedures for construction of various plasmids in Reference Example 2 are outlined in FIG. 8.

Figure 9:
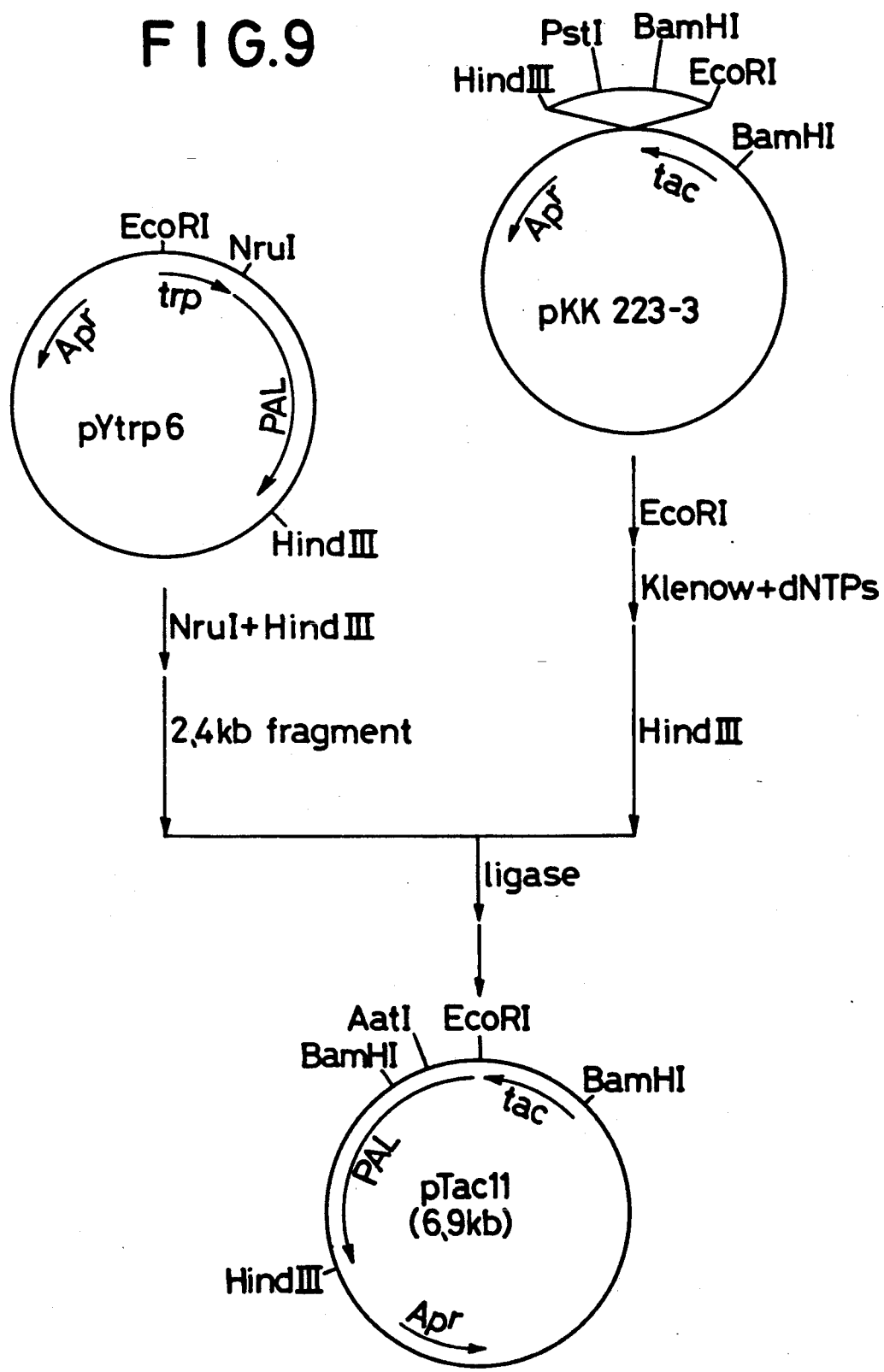
FIGS. 9, 10 and 11 illustrate detailed steps in process of constructing the hybrid plasmids pTac11, pP$_L$-PAL-head and pSW115, respectively.

(1) Construction of Plasmid pTac11 according to the Procedure Illustrated in FIG. 9

Firstly, the plasmid pYtrp6 was extracted from the E. coli MT-10414 (FERM BP-1712) carrying the pYtrp6 with an insertion therein of the structure gene for PAL obtained from Rhodosporidium toruloides according to the method described in Reference example 1. The plasmid thus obtained was digested with the restriction endonucleases NruI and HindIII. After electrophoresis, a DNA fragment having a size of 2.4 kb was obtained.

Separately, the plasmid pKK223-3 (Pharmacia Co.) carrying the tac promoter was digested with the restriction endonuclease EcoRI to obtain a DNA fragment having cohesive ends. The DNA fragment was then treated with DNA polymerase I to change the cohesive ends thereof to flush ends.

Thereafter, the flush-ended DNA fragment was digested with the restriction endonuclease HindIII to obtain a DNA fragment having cohesive ends. This DNA fragment was then ligated with the previously prepared 2.4 kb DNA fragment in the presence of T4 DNA ligase. The resultant product was introduced into E. coli (MC-1061) according to the method of Cohen et al. [Cohen, S. N., et al., Proc. Natl. Acad. Sci. USA, 69, 2110 (1982)].

Subsequently, the E. coli carrying the product introduced was grown on an ampicillin plate prepared by adding 1.5% agar to the aforementioned LB medium supplemented with ampicillin at a concentration of 50 micrograms/ml. After completion of the incubation, cloned cells were selected by virtue of ampicillin resistance and then plasmid molecules were extracted from the clones. The endonuclease cleavage map of the individual plasmid was constructed and consequently, the clone carrying the desired plasmid pTac11 having the structure illustrated in FIG. 9 was identified and the pTac11 was prepared from the cloned cells.

Figure 10:
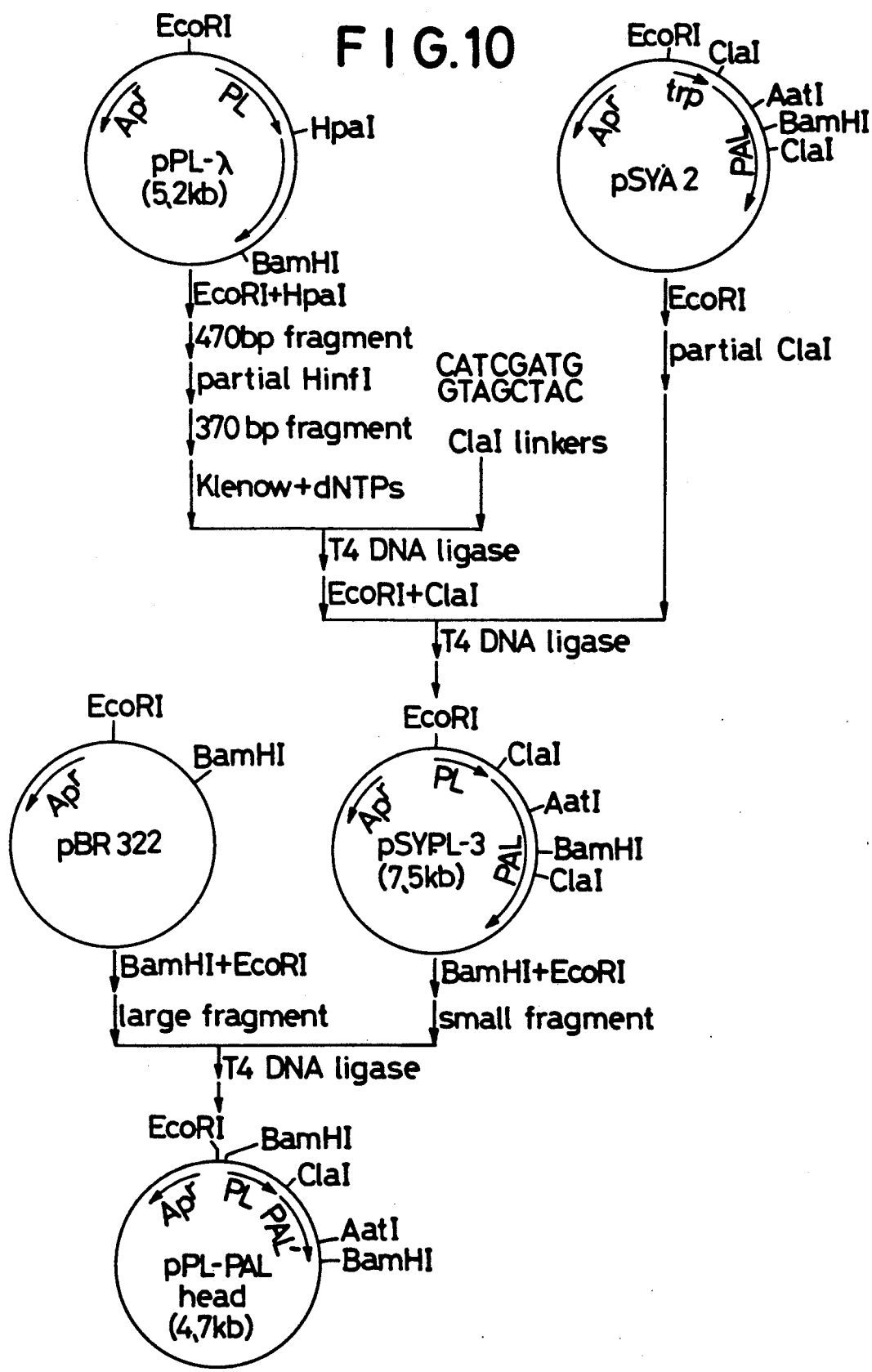

(2) Construction of Plasmid pP$_L$-PAL-head according to the Procedure Illustrated in FIG. 10

The plasmid pP$_L$-lambda (Pharmacia Co.) was digested with the restriction endonucleases EcoRI and HpaI. After electrophoresis, a DNA fragment of 470 bp was obtained. This 470 bp DNA fragment was partially digested with the restriction endonuclease HinfI. After electrophoresis, a DNA fragment of 370 bp was obtained.

Furthermore, the 370 bp DNA fragment was treated with DNA polymerase I to produce flush ends at 5'-termini thereof. The flush-ended DNA fragment thus prepared was allowed to react with ClaI linkers in the presence of T4 DNA ligase. After completion of the reaction, the resultant product was digested with the restriction endonucleases EcoRI and ClaI to obtain a fraction containing a mixture of large and small EcoRI-ClaI DNA fragments.

Separately, the plasmid pSYA2, which had been constructed in the process of cloning the structure gene for PAL of Rhodosporidium toruloides in Reference Example 1, was digested with the restriction endonuclease EcoRI. The resultant DNA fragment was further partially digested with the restriction endonuclease ClaI. After electrophoresis, a large DNA fragment was separately obtained from a mixture of large and small EcoRI-ClaI DNA fragments.

The large DNA fragment thus obtained from the plasmid pSYA2 was allowed to react in the presence of T4 DNA ligase with the previously prepared fraction containing the mixture of large and small EcoRI-ClaI fragments. The resultant reaction products were introduced into E. coli (MC-1061), and the E. coli cells were grown on an ampicillin plate. After completion of the incubation, colonies were selected by virtue of ampicillin resistance and then a plasmid molecule was extracted from the individual cloned cell. The endonuclease cleavage map of the individual plasmid molecule was constructed. Consequently, the clone carrying the desired plasmid pSYP$_L$-3 having the structure illustrated in FIG. 10 was identified and the plasmid pSYP$_L$-3 was prepared from the cells derived from this clone.

This clone was named MT-10424 (FERM BP-1714).

Furthermore, the plasmid pSYP$_L$-3 thus obtained was digested with the restriction endonucleases EcoRI and BamHI. After electrophoresis, a small DNA fragment was obtained from the resultant mixture of large and small EcoRI-BamHI fragments.

Separately, the plasmid pBR322 (Pharmacia Co.) was digested with the restriction endonucleases EcoRI and BamHI. A large DNA fragment was separately obtained from the resultant mixture of large and small EcoRI-BamHI DNA fragments after electrophoresis. The large DNA fragment thus obtained from the plasmid pBR322 was then allowed to react in the presence of T4 DNA ligase with the small fragment previously prepared from the plasmid pSYP$_L$-3. Consequently, plasmid pP$_L$-PAL-head having the structure illustrated in FIG. 10 was obtained. In order to confirm that the desired plasmid was obtained, the resultant product of the aforementioned reaction in the presence of T4 DNA ligase was introduced into E. coli (MC-1061) and then the E. coli cells were grown on an ampicillin plate. Cloned cells were selected by virtue of the ampicillin resistance and then a plasmid molecule was extracted from the clones. The endonuclease cleavage map of the individual plasmid was constructed to verify the presence of the desired plasmid.

Figure 11:
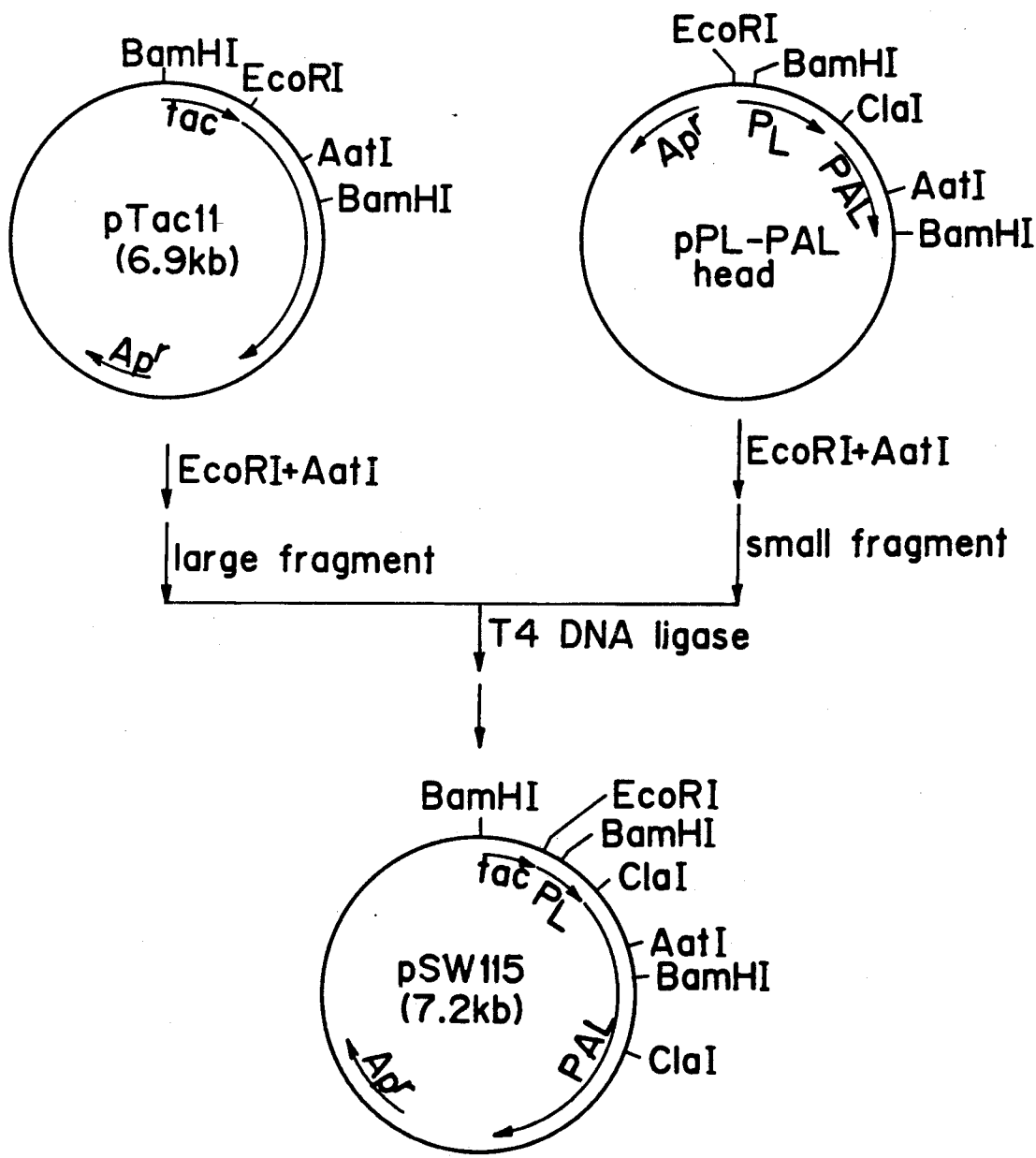

(3) Construction of Plasmid pSW115 According to the Procedure Illustrated in FIG. 11

Firstly, the plasmid pTac11 obtained in Section (1) above was digested with the restriction endonucleases EcoRI and AatI. After electrophoresis, a large DNA fragment was separately obtained from a mixture of large and small EcoRI-AatI DNA fragments.

Separately, the plasmid pP$_L$-PAL-head obtained in section (2) above was digested with the restriction endonucleases EcoRI and AatI. After electrophoresis, a small DNA fragment was separately obtained from a mixture of large and small EcoRI-AatI DNA fragments.

Finally, the aforementioned large DNA fragment derived from the plasmid pTac11 was joined to the aforementioned small DNA fragment derived from the plasmid pP$_L$-PAL-head by ligation with T4 DNA ligase. The plasmid pSW115 was thus obtained.

In order to confirm that the desired plasmid was obtained, the plasmid produced by the aforementioned reaction was introduced into E. coli (MC-1061) and the resultant transformants were selected on an ampicillin plate. A plasmid molecule was extracted from the individual cloned cell and the endonuclease cleavage map of the plasmid molecule was constructed. At the same time, the transformant was tested for the PAL activity according to the procedure described hereinafter. The transformed strain of E. coli having the PAL activity thus obtained was named MT-10423 (FERM BP1713).

(4) Expression of PAL by Using Plasmid pSW115

The transformed cell of E. coli carrying the plasmid pSW115 therein obtained in Section (3) above was inoculated into LB medium (pH 7.5) supplemented with ampicillin at a concentration of 50 micrograms/ml as aforementioned. The inoculated medium was incubated with shaking at 30° C. for 20 hours.

After completion of the incubation, the culture exhibited such a cell concentration as to give an optical density (O.D. at 660 nm) of 5.40. The cells were collected from the culture by centrifugation and then tested for the PAL activity according to the procedure described hereinafter. The specific activity of the cells thus obtained was 630 U/g cells (dry weight).

Determination of PAL Activity

The PAL activity of the cell extract was determined as follows by using the enzymatic reaction in which cinnamic acid is synthesized from L-phenylalanine.

First, cells were recovered from the culture by centrifugation. The collection cells were washed by suspending them in a 0.85% sodium chloride solution and recovered by centrifugation. The washed cells were then suspended in a 25 mM Tris-HCl buffer solution (pH 8.8) to give a cell concentration of about 1% by wet weight. The suspension was added to an enzymatic reaction medium comprising a 25 mM Tris-HCl buffer solution (pH 8.8) supplemented with 25 mM L-phenylalanine and 0.005% cetyl pyridium hydrochloride. The resultant reaction medium was incubated at 30° C. for 20 minutes. After the reaction was terminated by addition of 1N HCl, cinnamic acid formed in the reaction mixture was analyzed by liquid chromatography to estimate the PAL activity. One unit (U) as defined herein corresponds to the amount of enzyme to produce one micromole of cinnamic acid per minute.

The amount of the cells used for the calculation was the dry weight of the corresponding washed cells.

In the above Reference Examples, the introduction of the recombinant plasmid in E. coli was carried out according to the method of Cohen et al. [Cohen, S. N., et al., Proc. Natl. Acad. Sci. USA, 69, 2110 (1982)]. Unless otherwise specified, plasmids or DNA fragments were treated with restriction endonucleases, T4 DNA ligase or DNA polymerase I in usual manners and the preparations of plasmids from bacterial cells were carried out in conventional manners and further the restriction endonucleases, linkers, T4 DNA ligase and DNA polymerase I used were products of Takara Shuzo K.K.

EXAMPLES AND COMPARATIVE EXAMPLES

The present invention will be explained by the following Examples and Comparative Examples.

Media hereinafter used in Examples and Comparative Examples were prepared as follows.

LB-AP Medium

LB medium consisting of the following constituents was autoclaved at 120° C. for 15 minutes and was aseptically supplemented with ampicillin (AP) at a concentration of 50 micrograms/ml.

| LB medium component | |
|---|---|
| Tryptone | 10 g |
| Yeast extract | 5 g |
| NaCl | 5 g |
| Distilled water | 1 l |
| (The pH of the medium was adjusted to 7.5 with KOH) | |

LB-AP Agar Medium

LB medium consisting of the aforementioned constituents was supplemented with glucose and agar at a concentration of 15 g/l and 1 g/l, respectively. After sterilization by autoclaving, the medium was aseptically supplemented with ampicillin at a concentration of 100 micrograms/ml and then dispensed into petri dishes to prepare LB-AP agar medium plates.

| Synthetic medium: | |
|---|---|
| Monopotassium phosphate | 3 g |
| Dipotassium phosphate | 7 g |
| Magnesium sulfate.7H$_2$O | 0.5 g |
| Ammonium sulfate | 1.5 g |
| Calcium chloride.H$_2$O | 0.02 g |
| Ferrous sulfate.7H$_2$O | 0.02 g |
| Sodium citrate | 1 g |
| Casamino Acids | 12 g |
| L-tryptophan | 0.1 g |
| Distilled water | 1 l |

EXAMPLE 1

The culture of E. coli MT-10424 (FERM BP1714) carrying the hybrid plasmid pSYP$_L$-3 introduced therein was spread on an LB-AP agar medium plate and incubated at 37° C. The hybrid plasmid pSYP$_L$-3, having been constructed in the course of Reference Example 2, comprises the expression vector carrying the gene encoding for ampicillin resistance with the insertions of the P$_L$lambda promoter/operator and the PAL structure gene being inserted at the downstream of the P$_L$lambda promoter/operator region.

Separately, LB media containing glucose at five different concentrations as indicated in Table 2 were prepared, one each in a volume of 100 ml in a Sakaguchi flask with a cotton plug. After sterilization by autoclaving, ampicillin was aseptically added to the medium in each flask at a concentration of 50 micrograms/ml to prepare LB-AP medium.

Subsequently, a portion of the bacterial cells taken from a colony appeared on the LB-AP agar medium plate was transferred as an inoculum into each LB-AP medium in the Sakaguchi flask. The inoculated media were then incubated at 30° C. for 25 hours with shaking at 110 strokes per minute.

After the incubation, cell extracts were prepared from the cultures and tested for the PAL activity in the manner as described hereinafter.

The bacterial growth estimated by $OD_{600}$ and the PAL specific activity of the individual culture at the end of the incubation are shown in Table 2.

Preparation of Cellular Extract

Cells were recovered from the individual culture by centrifugation and then suspended and washed in a 0.85% NaCl solution. The washed cells were recovered again by centrifugation, suspended in a 0.05 mM Tris-HCl buffer solution (pH 8.8) at a cell concentration of 2% by wet weight and then subjected to ultrasonic treatment to destruct the cells. Resultant cell debris in the suspension was removed by centrifugation to prepare the cellular extract.

Determination of PAL Activity

The PAL activity of the cell extract was determined as follows by using the enzymatic reaction in which cinnamic acid is synthesized from L-phenylalanine.

First, a sample of a cell extract was diluted with a 25 mM Tris-HCl buffer solution (pH 8.8) to give a cell concentration of about 1% by wet weight and a 1.0 ml portion thereof was added to 4.0 ml of a 31.25 mM Tris-HCl buffer solution (pH 8.8) supplemented with 31.25 mM L-phenylalanine. The resultant solution was allowed to react at 30° C. for 20 minutes and then the reaction was terminated by addition of 1 ml of 1N-HCl. The amount of cinnamic acid produced in the reaction mixture was determined by liquid chromatography under the conditions as hereinafter described to estimate the PAL activity.

One unit (U) as defined herein is the amount of the enzyme to produce one micromole of cinnamic acid per minute.

Conditions for Liquid Chromatography

An isolation column, YMC Pack A-312 (Yamamura Chemical Laboratories, Japan), was used with a mobile phase of methanol:water:phosphoric acid (50:41:0.08 v/v) and cinnamic acid was detected with an ultraviolet spectrophotometer at the detection wave length of 260 nm.

The amount of the cells used for the calculation of the PAL specific activity was the dry weight of the corresponding washed cells.

TABLE 2

| No. | 1 | 2 | 3 | 4 | 5 |
|---|---|---|---|---|---|
| Glucose (%) | 0 | 0.03 | 0.10 | 0.30 | 1.00 |
| Bacterial growth ($OD_{600}$) | 2.8 | 3.9 | 5.8 | 6.7 | 6.1 |
| PAL specific activity (U/g dry cell) | 137 | 140 | 146 | 27 | 10 |

As is evident from Table 2, the *E. coli* cells grown in the medium containing glucose at a concentration of 0.3% or more grew better and exhibited lower PAL specific activity than those grown in the medium containing less than 0.3% glucose. In other words, the genes for PAL was poorly expressed in the medium containing glucose at a concentration of 0.3% or more. Thus, it was confirmed that by making the glucose concentration 0.3% or more, gene expression was effectively controlled.

EXAMPLE 2

The culture of *E. coli* MT-10414 (FERM BP1712) carrying the hybrid plasmid pYtrp6 introduced therein was spread on an LB-AP agar medium plate and the plate was incubated at 37° C. The plasmid pYtrp6, having been obtained in the course of Reference Example 1, comprises the expression vector carrying the gene encoding for ampicillin resistance with the insertions of the trp promoter and the PAL structure gene being inserted at the downstream of the trp promoter. Subsequently, the bacterial cells taken from a colony appeared on the LB-AP agar medium plate were dispensed in an approximately equal amount each as an inoculum into LB media having been supplemented with ampicillin at a concentration of 50 micrograms/ml and containing five different concentrations as indicated in Table 3, one each in a volume of 5 ml in a test tube with a cotton plug. The tubes were then incubated at 30° C. for 25 hours with shaking at 100 strokes per minute.

After the incubation, cell extracts were prepared from the cultures and tested for the PAL activity in the same manner as described in Example 1.

The bacterial cell concentration (measured at $OD_{600}$) and the PAL specific activity of the cultures at the end of the incubation are shown in Table 3.

TABLE 3

| No. | 1 | 2 | 3 | 4 | 5 |
|---|---|---|---|---|---|
| Glucose (%) | 0 | 0.03 | 0.10 | 0.30 | 1.00 |
| Bacterial growth ($OD_{600}$) | 2.2 | 3.1 | 4.3 | 4.9 | 4.5 |
| PAL specific activity (U/g dry cell) | 167 | 164 | 225 | 64 | 40 |

As is evident from the results in Table 3, in the medium containing glucose at a concentration of 0.3% or more, the growth of *E. coli* was sufficient while the PAL specific activity thereof was substantially suppressed in this Example 2, similarly to Example 1 above.

EXAMPLE 3

The culture of *E. coli* MT-10423 (FERM BP1713) carrying the hybrid plasmid pSW115 introduced therein was spread on an LB-AP agar medium plate and incubated at 37° C. The hybrid plasmid pSW115, having been constructed in the course of Reference Example 2, comprises the expression vector carrying the gene encoding for ampicillin resistance with the insertions of the combined promoter comprising the tac promoter and the $P_L$ lambda promoter linking at the downstream of said tac promoter and the PAL structure gene being inserted at the downstream of the combined promoter.

Separately, twelve portions of LB medium supplemented with ampicillin at a concentration of 50 micrograms/ml were prepared, one each in a volume of 5 ml containing one of sugar components, glucose, mannose, maltose or sorbitol, at a concentration of 0.1, 0.3 or 1.0% as indicated in Table 4.

To each medium thus prepared, bacterial cells taken from a colony on the LB-AP agar medium plate were dispensed in an approximately equal amount as an inoculum. The inoculated media were incubated at 30° C. for 24 hours with shaking at 110 strokes per minute.

After completion of the culture, the cultured cells were treated in the same manner as described in Example 1 and subjected to the determination of the PAL activity.

Table 4 shows bacterial growth indicated by $OD_{600}$ of the culture at the end of the incubation and the PAL specific activity of the bacterial cells thereof.

TABLE 4

| Carbon source | Glucose | Maltose | Mannose | Sorbitol |
|---|---|---|---|---|
| | _____No._____ | | | |
| | 1 | 2 | 3 | 4 |
| Carbon source (%) | 0.1 | 0.1 | 0.1 | 0.1 |
| Bacterial growth ($OD_{600}$) | 5.5 | 5.0 | 4.8 | 5.2 |
| PAL specific activity (U/g dry cell) | 313 | 265 | 294 | 297 |
| | _____No._____ | | | |
| | 5 | 6 | 7 | 8 |
| Carbon source (%) | 0.3 | 0.3 | 0.3 | 0.3 |
| Bacterial growth ($OD_{600}$) | 5.2 | 5.9 | 5.3 | 6.0 |
| PAL specific activity (U/g dry cell) | 63 | 70 | 45 | 115 |
| | _____No._____ | | | |
| | 9 | 10 | 11 | 12 |
| Carbon source (%) | 1.0 | 1.0 | 1.0 | 1.0 |
| Bacterial growth ($OD_{600}$) | 5.1 | 6.3 | 5.4 | 6.4 |
| PAL specific activity (U/g dry cell) | 61 | 58 | 37 | 110 |

As is evident from Table 4, the PAL expression was efficiently suppressed in every culture with the sugar component at a concentration of 0.3% or more.

EXAMPLE 4

Firstly, 1.5 l of the synthetic medium was taken into a 2-l-volume jar for small scale fermentation equipped with an apparatus for the measurement of the glucose concentration in the culture medium. After autoclaving, 0.5% ampicillin was aseptically added to the medium.

Separately, 100 ml of the synthetic medium supplemented with glucose at a concentration of 1% was prepared in a Sakaguchi flask. After autoclaving, ampicillin at a concentration of 50 micrograms/ml was aseptically added to the medium. Subsequently, E. coli MT-10423 as used in Example 3 was inoculated into this medium and cultured at 30° C. for 22 hours with shaking at 110 strokes per minute to prepare a seed culture. Seventy-five milliliters of the seed culture was inoculated into the medium having been prepared in the fermentation jar as mentioned above. The medium with the inoculum was aseptically supplemented with 1% glucose and the pH thereof was adjusted to 7.0 by addition of aqueous ammonium. The culture thus obtained was incubated at 30° C. with aeration. The glucose concentration of the culture was maintained by continuously supplying glucose therein at the level of 1% until a desired number of cells be obtained. When the cell number reached the level as desired, the glucose supply was stopped and thereafter the glucose concentration of the culture decreased to the level of less than 0.3% due to the consumption by the bacteria so that PAL be expressed.

The culture fluids were taken at intervals during incubation so as to measure the glucose concentration and bacterial concentration ($OD_{660}$). At the same time, the PAL specific activity was determined in the same manner as described in Example 1. The results are shown in FIG. 12.

Figure 12:
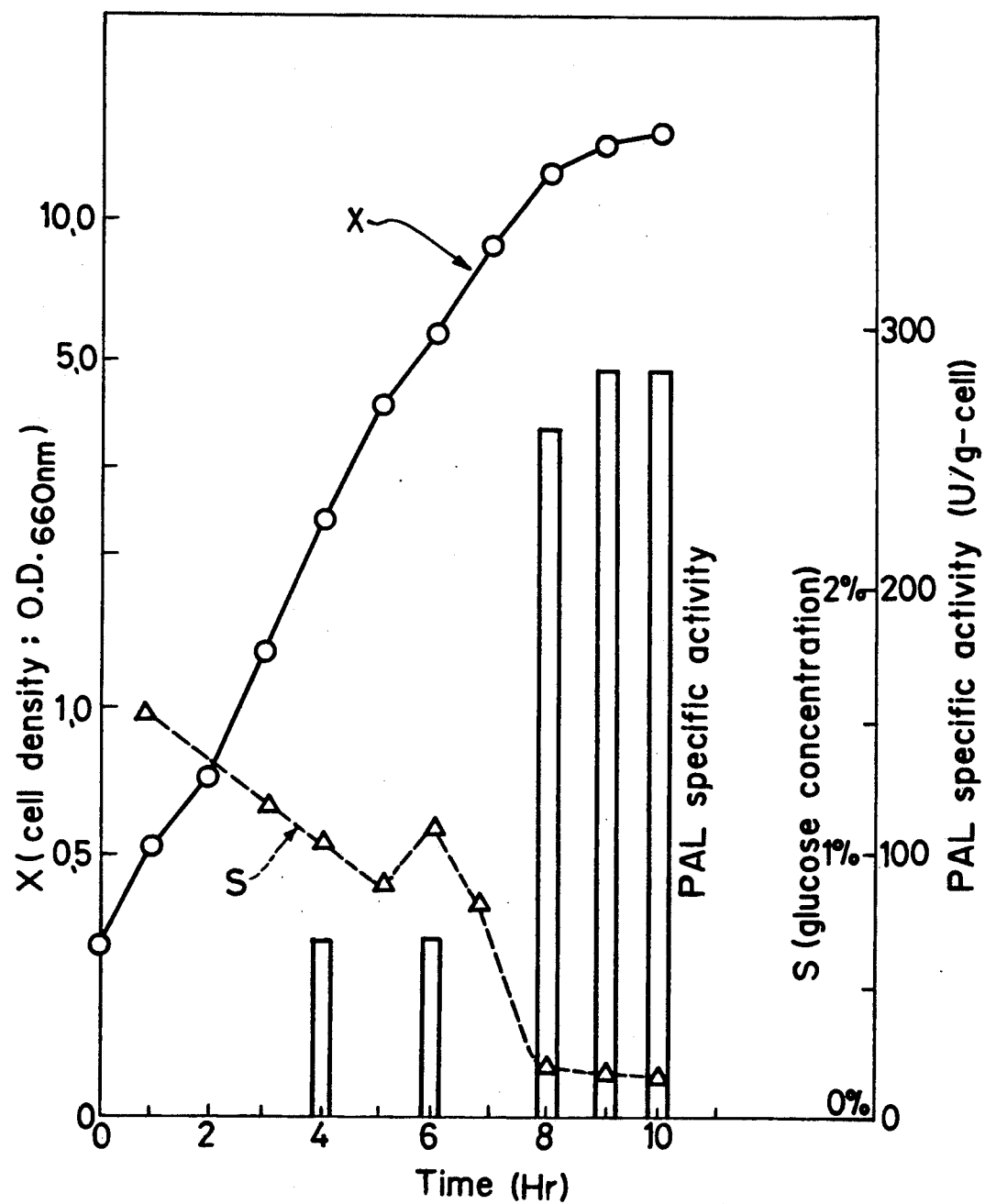
FIG. 12 is a graph showing changes in glucose and bacterial cell concentrations and the PAL specific activity of the cells in the course of the culture in Example 4.

As is evident from FIG. 12, when the concentration of glucose in the culture was less than 0.3%, expression of PAL proceeded efficiently so as to give sufficiently high PAL specific activity.

EXAMPLE 5

This figure shows three variables, cell density (X), glucose concentration (S) and PAL specific activity over a 10 hour (Hr) time period. In FIG. 12, cell density (X) is scaled on the left vertical axis an the line connecting the open circles (o) with the adjacent X and arrow shows the increase in cell density over time in hours measured on the horizontal axis. The right vertical axis (adjacent the outside of the axis) is PAL specific activity scaled in 0 to 300 units. PAL specific activity is shown in bars at time intervals of 4, 6, 8, 9 and 10 hours. The right vertical axis is also scaled for glucose concentration (S) (inside of the axis). Glucose concentration (S) (inside of the axis). Glucose concentration (S) is reported over time by the dashed line connecting the open triangles indicated by the arrow S.

The media to be used in this Example and Comparative Example 1 were prepared as follows:

LB Medium

To the constituents of the aforementioned glucose-free LB medium was added glucose at a concentration of 1 g/l. After autoclaving at 120° C. for 15 minutes, the medium was aseptically supplemented with ampicillin at a concentration of 50 micrograms/ml.

"A" Medium

To the constituents of the aforementioned glucose-free LB medium was added glucose at a concentration of 10 g/l. After autoclaving at 120° C. for 15 minutes, the medium was aseptically supplemented with ampicillin at a concentration of 50 micrograms/ml.

Firstly, the culture of E. coli MT-10423 as used in Example 3 carrying the hybrid plasmid pSW115 therein was plated on an LB-AP agar medium plate. After incubation at 37° C. for 16 hours, portions of the bacterial cells taken from a colony appeared on the LB-AP agar medium plate were inoculated into "A" medium and LB medium in a volume of 5 ml each in a test tube with a cotton plug. After culturing at 30° C. for 24 hours with shaking at 110 strokes per minute, cultures No. 1-1 (cultured in "A" medium) and No. 1-2 (cultured in LB medium) were obtained.

Subsequently, 15 microliters each of the culture 1-1 (including bacterial cells) were dispensed into "A" medium and LB medium in a volume of 5 ml each in a test tube with a cotton plug. After the incubation under the same conditions as described above, cultures No. 1-3 (cultured in "A" medium) and No. 1-4 (cultured in LB culture) were obtained.

Further, cultures No. 1-5, 1-6 and 1-7 were obtained by repeating the aforementioned procedures in the order as indicated in FIG. 13.

The cells of cultures No. 1-2, No. 1-4, No. 1-6 and No. 1-7 were collected by centrifugation immediately after the completion of the culture. The cells thus obtained were suspended and washed in a 0.85% NaCl solution and thereafter were recovered again by centrifugation and frozen for storage.

The frozen cells of the individual cultures thus having been stored were defrosted and subjected to the cell extract preparation in the same manner as described in Example 1. The PAL specific activity of the cell extracts were determined and the results are shown in Table 5.

COMPARATIVE EXAMPLE 1

Cultures of No. 2-1, No. 2-2, No. 2-3, No. 2-4, No. 2-5, No. 2-6 and No. 2-7 were obtained by repeating the same procedure as described in Example 5 in the order indicated in FIG. 14, except that LB medium was used in place of every "A" medium in the procedure Further, the cells of cultures No. 2-2, No. 2-4, No. 2-6 and No. 2-7 were subjected to the freezing for storage and then to the preparation of cell extracts in the manner as described in Example 5. The PAL specific activity of the cultures were determined and the results are shown in Table 5.

TABLE 5

| Culture No. | Example 5 | | | | Comparative Example 1 | | | |
|---|---|---|---|---|---|---|---|---|
|  | 1-2 | 1-4 | 1-6 | 1-7 | 2-2 | 2-4 | 2-6 | 2-7 |
| PAL specific activity of the cells grown on LB medium for expression (U/g dry cells) | 301 | 334 | 340 | 270 | 300 | 120 | 25 | 20 |

Among the above-mentioned strains, those having an ATCC number have been deposited with the American Type Culture Collection, 12301 Parklawn Drive, Rockville, Md. 20852-1776, U.S.A.; that having an IFO number with the Fermentation Research Institute (Incorporated Foundation), 17-85, Juso-Motomachi 2-chome, Yodogawa-ku, Osaka City, Japan; and those having an FERM number with the Fermentation Research Institute of the Agency of Industrial Science and Technology, 1-3, Higashi 1-chome, Tsukuba-shi, Ibaraki-ken, 305, Japan.

Those having an ATCC number and that having an IFO number are publicly available.

Those having an FERM number were deposited on the following date for patent purposes by the applicant.

FERM BP-1710 on Jul. 4, 1986;
FERM BP-1712 on Jul. 26, 1986;
FERM BP-1713 on Oct. 31, 1986; and
FERM BP-1714 on Oct. 31, 1986.

What is claimed is:

1. A process for producing L-phenylalanine ammonialyase derived from *Rhodosporidium toruloides* by culturing an *Escherichia coli* carrying a promoter which is either a $P_L$ lambda promoter or a combined promoter containing both the tac promoter and the $P_L$ promoter, and a foreign structural gene encoding for L-phenylalanine ammonialyase derived from *Rhodosporidium toruloides* linked to said promoter so as to permit expression of said foreign structural gene under the direction of said promoter, which process comprises steps of:
   (a) culturing said *E. coli* in a culture medium containing a sugar component and a carbon source, in which the concentration of the sugar component is maintained at least 0.3%, and thereafter
   (b) culturing said *E. coli* grown in said first culture process, in which the concentration of said sugar component in the second culture medium is maintained at less than 0.3%.

2. A process of producing a foreign gene product as set forth in claim 1, wherein said L-phenylalanine ammonialyase has the amino acid sequence as follows:

| | | | | | | | | | |
|---|---|---|---|---|---|---|---|---|---|
| 1 | | | | | | | | | 10 |
| Met | Ala | Pro | Ser | Leu | Asp | Ser | Ile | Ser | His |
| 11 | | | | | | | | | 20 |
| Ser | Phe | Ala | Asn | Gly | Val | Ala | Ser | Ala | Lys |
| 21 | | | | | | | | | 30 |
| Gln | Ala | Val | Asn | Gly | Ala | Ser | Thr | Asn | Leu |
| 31 | | | | | | | | | 40 |
| Ala | Val | Ala | Gly | Ser | His | Leu | Pro | Thr | Thr |
| 41 | | | | | | | | | 50 |
| Gln | Val | Thr | Gln | Val | Asp | Ile | Val | Glu | Lys |
| 51 | | | | | | | | | 60 |
| Met | Leu | Ala | Ala | Pro | Thr | Asp | Ser | Thr | Leu |
| 61 | | | | | | | | | 70 |
| Glu | Leu | Asp | Gly | Tyr | Ser | Leu | Asn | Leu | Gly |
| 71 | | | | | | | | | 80 |
| Asp | Val | Val | Ser | Ala | Ala | Arg | Lys | Gly | Arg |
| 81 | | | | | | | | | 90 |
| Pro | Val | Arg | Val | Lys | Asp | Ser | Asp | Glu | Ile |
| 91 | | | | | | | | | 100 |
| Arg | Ser | Lys | Ile | Asp | Lys | Ser | Val | Glu | Phe |
| 101 | | | | | | | | | 110 |
| Leu | Arg | Ser | Gln | Leu | Ser | Met | Ser | Val | Tyr |
| 111 | | | | | | | | | 120 |
| Gly | Val | Thr | Thr | Gly | Phe | Gly | Gly | Ser | Ala |
| 121 | | | | | | | | | 130 |
| Asp | Thr | Arg | Thr | Glu | Asp | Ala | Ile | Ser | Leu |
| 131 | | | | | | | | | 140 |
| Gln | Lys | Ala | Leu | Leu | Glu | His | Gln | Leu | Cys |
| 141 | | | | | | | | | 150 |
| Gly | Val | Leu | Pro | Ser | Ser | Phe | Asp | Ser | Phe |
| 151 | | | | | | | | | 160 |
| Arg | Leu | Gly | Arg | Gly | Leu | Glu | Asn | Ser | Leu |
| 161 | | | | | | | | | 170 |
| Pro | Leu | Glu | Val | Val | Arg | Gly | Ala | Met | Thr |
| 171 | | | | | | | | | 180 |
| Ile | Arg | Val | Asn | Ser | Leu | Thr | Arg | Gly | His |
| 181 | | | | | | | | | 190 |
| Ser | Ala | Val | Arg | Leu | Val | Val | Leu | Glu | Ala |
| 191 | | | | | | | | | 200 |
| Leu | Thr | Asn | Phe | Leu | Asn | His | Gly | Ile | Thr |
| 201 | | | | | | | | | 210 |
| Pro | Ile | Val | Pro | Leu | Arg | Gly | Thr | Ile | Ser |
| 211 | | | | | | | | | 220 |
| Ala | Ser | Gly | Asp | Leu | Ser | Pro | Leu | Ser | Tyr |
| 221 | | | | | | | | | 230 |
| Ile | Ala | Ala | Ala | Ile | Ser | Gly | His | Pro | Asp |
| 231 | | | | | | | | | 240 |
| Ser | Lys | Val | His | Val | Val | His | Glu | Gly | Lys |
| 241 | | | | | | | | | 250 |
| Glu | Lys | Ile | Leu | Tyr | Ala | Arg | Glu | Ala | Met |
| 251 | | | | | | | | | 260 |
| Ala | Leu | Phe | Asn | Leu | Glu | pro | Val | Val | Leu |
| 261 | | | | | | | | | 270 |

-continued

| | | | | | | | | | |
|---|---|---|---|---|---|---|---|---|---|
| | Gly | Pro | Lys | Glu | Gly | Leu | Gly | Leu | Val | Asn |
| 271 | Gly | Thr | Ala | Val | Ser | Ala | Ser | Met | Ala | 280 Thr |
| 281 Leu | Ala | Leu | His | Asp | Ala | His | Met | Leu | 290 Ser |
| 291 Leu | Leu | Ser | Gln | Ser | Leu | Thr | Ala | Met | 300 Thr |
| 301 Val | Glu | Ala | Met | Val | Gly | His | Ala | Gly | 310 Ser |
| 311 Phe | His | Pro | Phe | Leu | His | Asp | Val | Thr | 320 Arg |
| 321 Pro | His | Pro | Thr | Gln | Ile | Glu | Val | Ala | 330 Gly |
| 331 Asn | Ile | Arg | Lys | Leu | Leu | Glu | Gly | Ser | 340 Arg |
| 341 Phe | Ala | Val | His | His | Glu | Glu | Glu | Val | 350 Lys |
| 351 Val | Lys | Asp | Asp | Glu | Gly | Ile | Leu | Arg | 360 Gln |
| 361 Asp | Arg | Tyr | Pro | Leu | Arg | Thr | Ser | Pro | 370 Gln |
| 371 Trp | Leu | Gly | Pro | Leu | Val | Ser | Asp | Leu | 380 Ile |
| 381 His | Ala | His | Ala | Val | Leu | Thr | Ile | Glu | 390 Ala |
| 391 Gly | Gln | Ser | Thr | Thr | Asp | Asn | Pro | Leu | 400 Ile |
| 401 Asp | Val | Glu | Asn | Lys | Thr | Ser | His | His | 410 Gly |
| 411 Gly | Asn | Phe | Gln | Ala | Ala | Ala | Val | Ala | 420 Asn |
| 421 Thr | Met | Glu | Lys | Thr | Arg | Leu | Gly | Leu | 430 Ala |
| 431 Gln | Ile | Gly | Lys | Leu | Asn | Phe | Thr | Gln | 440 Leu |
| 441 Thr | Glu | Met | Leu | Asn | Ala | Gly | Met | Asn | 450 Arg |
| 451 Gly | Leu | Pro | Ser | Cys | Leu | Ala | Ala | Glu | 460 Asp |
| 461 Pro | Ser | Leu | Ser | Tyr | His | Cys | Lys | Gly | 470 Leu |
| 471 Asp | Ile | Ala | Ala | Ala | Ala | Tyr | Thr | Ser | 480 Glu |
| 481 Leu | Gly | His | Leu | Ala | Asn | Pro | Val | Thr | 490 Thr |
| 491 His | Val | Gln | Pro | Ala | Glu | Met | Ala | Asn | 500 Gln |
| 501 Ala | Val | Asn | Ser | Leu | Ala | Leu | Ile | Ser | 510 Ala |
| 511 Arg | Arg | Thr | Thr | Glu | Ser | Asn | Asp | Val | 520 Leu |
| 521 Ser | Leu | Leu | Leu | Ala | Thr | His | Leu | Tyr | 530 Cys |
| 531 Val | Leu | Gln | Ala | Ile | Asp | Leu | Arg | Ala | 540 Ile |
| 541 Glu | Phe | Glu | Phe | Lys | Lys | Gln | Phe | Gly | 550 Pro |
| 551 Ala | Ile | Val | Ser | Leu | Ile | Asp | Gln | His | 560 Phe |
| 561 Gly | Ser | Ala | Met | Thr | Gly | Ser | Asn | Leu | 570 Arg |
| 571 Asp | Glu | Leu | Val | Glu | Lys | Val | Asn | Lys | 580 Thr |
| 581 Leu | Ala | Lys | Arg | Leu | Glu | Gln | Thr | Asn | 590 Ser |
| 591 Tyr | Asp | Leu | Val | Pro | Arg | Trp | His | Asp | 600 Ala |
| 601 Phe | Ser | Phe | Ala | Ala | Gly | Thr | Val | Val | 610 Glu |
| 611 Val | Leu | Ser | Ser | Thr | Ser | Leu | Ser | Leu | 620 Ala |
| 621 Ala | Val | Asn | Ala | Trp | Lys | Val | Ala | Ala | 630 Ala |
| 631 Glu | Ser | Ala | Ile | Ser | Leu | Thr | Arg | Gln | 640 Val |
| 641 Arg | Glu | Thr | Phe | Trp | Ser | Ala | Ala | Ser | 650 Thr |
| 651 Ser | Ser | Pro | Ala | Leu | Ser | Tyr | Leu | Ser | 660 Pro |
| 661 Arg | Thr | Gln | Ile | Leu | Tyr | Ala | Phe | Val | 670 Arg |
| 671 Glu | Glu | Leu | Gly | Val | Lys | Ala | Arg | Arg | 680 Gly |
| 681 Asp | Val | Phe | Leu | Gly | Lys | Gln | Glu | Val | 690 Thr |
| 691 Ile | Gly | Ser | Asn | Val | Ser | Lys | Ile | Tyr | 700 Glu |
| 701 Ala | Ile | Lys | Ser | Gly | Arg | Ile | Asn | Asn | 710 Val |
| 711 Leu | Leu | Lys | Met | 716 Leu | Ala | | | | |

3. A process of producing a foreign gene product as set forth in claim 1, wherein said *E. coli* is *E. coli* MT-10424 which is obtained by transforming *Escherichia coli* MC1061 with plasmid pSYP$_L$-3.

4. A process of producing a foreign gene product as set forth in claim 1, wherein said *E. coli* is *E. coli* MT-10423 which is obtained by transforming *Escherichia coli* MC1061 with plasmid pSW115.

* * * * *